(12) United States Patent
Wagner et al.

(10) Patent No.: US 10,391,093 B2
(45) Date of Patent: *Aug. 27, 2019

(54) THERAPEUTIC COMPOUNDS

(71) Applicant: Arizona Board of Regents, A Body Corporate of the State of Arizona, Acting For and On Behalf of Arizona State University, Scottsdale, AZ (US)

(72) Inventors: Carl E. Wagner, Glendale, AZ (US); Peter W. Jurutka, Scottsdale, AZ (US); Pamela A. Marshall, Peoria, AZ (US)

(73) Assignee: ARIZONA BOARD OF REGENTS, A BODY CORPORATE OF THE STATE OF ARIZONA, ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 19 days.

This patent is subject to a terminal disclaimer.

(21) Appl. No.: 15/398,584

(22) Filed: Jan. 4, 2017

(65) Prior Publication Data

US 2017/0182046 A1 Jun. 29, 2017

Related U.S. Application Data

(63) Continuation of application No. 14/344,867, filed as application No. PCT/US2012/055186 on Sep. 13, 2012, now Pat. No. 9,573,906.

(Continued)

(51) Int. Cl.
C07D 239/28 (2006.01)
C07D 213/55 (2006.01)

(Continued)

(52) U.S. Cl.
CPC ............ *A61K 31/505* (2013.01); *C07C 57/50* (2013.01); *C07C 57/62* (2013.01); *C07C 59/54* (2013.01);

(Continued)

(58) Field of Classification Search
None
See application file for complete search history.

(56) References Cited

U.S. PATENT DOCUMENTS

| 4,762,844 A | 8/1988 | Grohe et al. |
| 5,780,676 A | 7/1998 | Boehm et al. |

(Continued)

FOREIGN PATENT DOCUMENTS

| EP | 0637297 B1 | 8/2000 |
| EP | 1180520 A1 | 2/2002 |

(Continued)

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological, pp. 101-113.*

(Continued)

*Primary Examiner* — Kathrien A Cruz
*Assistant Examiner* — Andrew P Lee
(74) *Attorney, Agent, or Firm* — Viksnins Harris Padys Malen LLP

(57) ABSTRACT

The invention provides compounds of formulae I, II, III, and IV:

(Continued)

US 10,391,093 B2

Page 2

| | | | |
|---|---|---|---|
| 2003/0135053 A1 | 7/2003 | Bernardon | |
| 2010/0010084 A1 | 1/2010 | Yu | |
| 2011/0253936 A1 | 10/2011 | Kurisawa et al. | |

FOREIGN PATENT DOCUMENTS

| | | | |
|---|---|---|---|
| JP | H11343263 A | 12/1999 | |
| JP | 2001522350 A | 11/2001 | |
| JP | 2002515025 A | 5/2002 | |
| WO | 1993021146 A1 | 10/1993 | |
| WO | 1999056740 A1 | 11/1999 | |
| WO | 2002018361 A2 | 3/2002 | |
| WO | 2004058762 A1 | 7/2004 | |
| WO | 2005058803 A1 | 12/2004 | |
| WO | 2005013949 A2 | 2/2005 | |
| WO | 2005058301 A1 | 6/2005 | |
| WO | 2005058798 A2 | 6/2005 | |
| WO | 2007022437 A2 | 2/2007 | |
| WO | 2008025965 A1 | 3/2008 | |
| WO | 2010096264 A2 | 8/2010 | |
| WO | 2011006157 A2 | 1/2011 | |
| WO | 2011103321 A1 | 8/2011 | |

OTHER PUBLICATIONS

Simone, Oncology: Introduction, Cecil Textbook of Medicine, 20th Edition, 1996 vol. 1, pp. 1004-1010.*
Adams, et al., "Discovery of GSK1070916, a Potent and Selective Inhibitor of Aurora B/C Kinase", J. Med. Chem. 53, 3973-4001 (2010).
Altucci, et al., "RAR and RXR modulation in cancer and metabolic disease", Nature Rev. Drug Discovery vol. 6, 793-810, (2007).
Boehm, et al., "Design and Synthesis of Potent Retinoid X Receptor Selective Ligands That Induce Apoptosis in Leukemia Cells", Journal of Medicinal Chemistry 38, 3146-55 (1995).
Boehm, et al., "Synthesis and Structure-Activity Relationships of Novel Retinoid X Receptor-Selective Retinoids", Journal of Medicinal Chemistry 37, 2930-2941 (1994).
Cesario, et al., "Differentiation and growth inhibition mediated via the RXR:PPARgamma heterodimer in colon cancer", Cancer Letters 240(2), 225-233 (2006).
Claudel, et al., "Reduction of atherosclerosis in apolipoprotein E knowout mice by activation of the retinoid X receptor", PNAS 98 (5), 2610-2615 (2001).
Cramer, et al., "ApoEdirected therapeutics rapidly clear β-amyloid and reverse deficits in AD mouse models", Science 335, 1503-1506 (2012).
Daiss, et al., "Crystal Structure Analysis, and Pharmacological Characterization of Disila-bexarotene, a Disila-Analogue of the RXR-Selective Retinoid Agonist Bexarotene", Organometallics 24, 3192-3199 (2005).
Dawson, et al., "Conformational effects on retinoid receptor selectivity. 2. Effects of retinoid bridging group on retinoid X receptor activity and selectivity", J. Med. Chem. 38, 3368-3383 (1995).
Dragnev, et al., "A Proof-of-Principle Clinical Trial of Bexarotene in Patients with Non-Small Cell Lung Cancer", Clin. Cancer Res. 13, 1794-1800 (2007).
Egea, et al., "Molecular recognition of agonist ligands by RXRs", Mol. Endocrinol. 16, 987-997 (2002).
European Examination Report, for corresponding EP Application No. 15154401.2, 5 pages, dated Nov. 9, 2016.
Farmer, et al., "Aza-retinoids as novel retinoid X receptor-specific agonists", Bioorg. Med. Chem. Lett. 16, 2352-2356 (2006).
Faul, et al., "Synthesis of Novel Retinoid X Receptor-Selective Retinoids", J. Org. Chem. 66, 5772-5782 (2001).
Feng-Ling, et al., "A Suzuki Coupling Approach to Trifluoromethyl Derivative of Targretin (LGD 1069)", Bioorganic and Medicinal Chemistry Letters, 7 (16), 2117-2120 (1997).
Field, et al., "LXR/RXR ligand activation enhances basolateral efflux of beta-sitosterol in CaCo-2 cells", J. Lipid Res. 45, 905-913 (2004).
Forman, et al., "Unique response pathways are established by allosteric interactions among nuclear hormone receptors", Cell 81, 541-550 (1995).

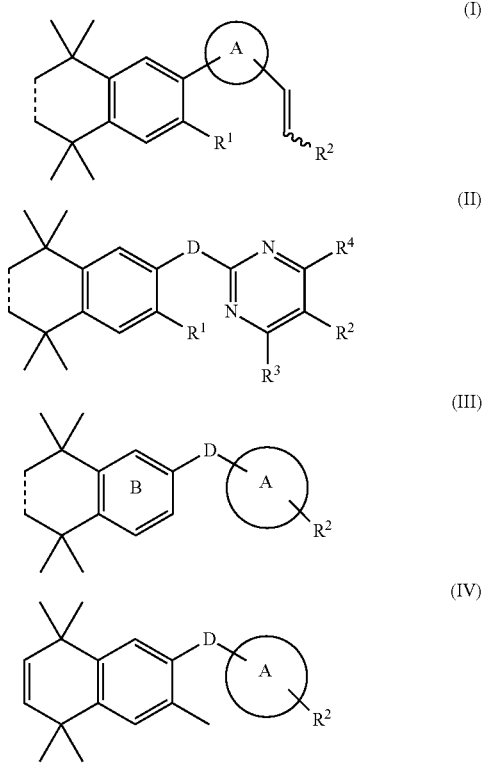

and salts thereof, as well as pharmaceutical compositions comprising such compounds. The compounds are useful for treating cancers and Alzheimer's disease.

8 Claims, 2 Drawing Sheets

Related U.S. Application Data

(60) Provisional application No. 61/535,311, filed on Sep. 15, 2011, provisional application No. 61/681,519, filed on Aug. 9, 2012.

(51) Int. Cl.
    C07C 57/50        (2006.01)
    A61K 31/505     (2006.01)
    C07C 57/62        (2006.01)
    C07D 213/80     (2006.01)
    C07C 59/54        (2006.01)

(52) U.S. Cl.
    CPC ......... C07D 213/55 (2013.01); C07D 213/80 (2013.01); C07D 239/28 (2013.01); C07C 2602/10 (2017.05)

(56) References Cited

U.S. PATENT DOCUMENTS

| | | |
|---|---|---|
| 5,962,731 A | 10/1999 | Boehm et al. |
| 6,137,002 A | 10/2000 | Fisher |
| 6,291,677 B1 | 9/2001 | Vasudevan |
| 6,303,785 B1 | 10/2001 | Vasudevan |
| 6,313,107 B1 | 11/2001 | Vasudevan |
| 7,655,699 B1 | 2/2010 | Boehm |
| 9,573,906 B2 | 2/2017 | Wagner et al. |

(56) References Cited

OTHER PUBLICATIONS

Garcia, et al., "Pyrazine arotinoids with inverse agonist activities on the retinoid and rexinoid receptors",CHEMBIOCHEM 10, 1252-1259 (2009).
Grenningloh, et al., "Cutting Edge: Inhibition of the Retinoid X Receptor (RXR) Blocks T Helper 2 Differentiation and Prevents Allergic Lung Inflammation", J. Immunol. 176, 5161-5166 (2006).
Jong, et al., "Conformational effects on retinoid recepetor selectivity. 1. Effect of 9-double bond geometry on retinoid X receptor activity", J. Med. Chem. 36, 2605-2613, (1993).
Jurutka, et al., "Modeling, synthesis, and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid (bexarotene) and (E)-3-(3-(1,2,3,4-tetrahydro-1,1,4,", Journal of Medicinal Chemistry 56, 8432-8454 (2013).
Kiick, et al., "Incorporation of azides into recombinant proteins for chemoselective modification by the Staudinger ligation", Proc. Natl. Acad. Sci. U.S.A. 99(1), 19-24 (2002).
Lehmann, et al., "Retinoids selective for retinoid X receptor pathways", Science 258, 1944-1946 (1992).
Leid, et al., "Multiplicity Generates Diversity in the Retinoic Acid Signaling Pathways", Trends Biochem. Sci. 17, 427-433 (1992).
Li, et al., "Functional Evidence for Retinoid X Receptor (RXR) as a Nonsilent Partner in the Thyroid Hormone Receptor/RXR Heterodimer", Mol. Cell. Biol. 22, 5782-5792 (2002).
Love, et al., "The structural basis for the specificity of retinoid-X receptor-selective agonists: new insights into the role of helix H12", J. Biol. Chem. 277(13), 11385-11391 (2002).
Mangelsdorf, et al., "A direct repeat in the cellular retinol-binding protein type II gene confers differential regulation by RXR and RAR", Cell 66, 555-561 (1991).
Mangelsdorf, et al., "The RXR heterodimers and orphan receptors", Cell 83, 841-850 (1995).
Marshall, "Using *Saccharomyces cerevisiae* to Test the Mutagenicity of Household Compounds: An Open Ended Hypothesis-Driven Teaching Lab", CBE-LSE 6, 307-315 (2007).
Michellys, "Design, synthesis and structure-activity relationship of novel RXR-selective modulators", Bioorg. Med. Chem. Lett. 14, 1593-1598 (2004).
Michellys, et al., "Design, synthesis, and structure-activity relationship studies of novel 6,7-locked-[7-(2-alkoxy-3,5-dialkylbenzene)-3-methylocta]-2,4,6-trienoic acids", Journal of Medicinal Chemistry 46, 4087-4103 (2003).
Michellys, et al., "Novel (2E,4E,6Z)-7-(2-alkoxy-3,5-dialkylbenzene)-3-methylocta-2,4,6-trienoic acid retinoid X receptor modulators are active in models of type 2 diabetes", Journal of Medicinal Chemistry 46, 2683-2696 (2003).
Morris, et al., "AutoDock4 and AutoDockTools4: Automated Docking with Selective Receptor Flexibility", J. Comput. Chem. 30(16), 2785-2791 (2009).
Mukherjee, et al., "Sensitization of diabetic and obese mice to insulin by retinoid X receptor agonists", Nature 386, 407-410 (1997).
Murthy, et al., "LXR/RXR activation enhances basolateral efflux of cholesterol in CaCo-2 cells", J. Lipid Res. 43, 1054-1064 (2002).
Nahoum, et al., "Modulators of the structural dynamics of the retinoid X receptor to reveal receptor function", Proc. Natl. Acad. Sci. 104, 17323-17328 (2007).
Nakatsuka, et al., "RXR antagonism induces G0/G1 cell cycle arrest and ameliorates obesity by up-regulating the p53-p21Cip1 pathway in adipocytes", The Journal of Pathology 226, 784-795 (2012).

O'Boyle, et al., "Open Babel: An open chemical toolbox", J. Cheminf. 3(33), 14 pages (2011).
Olefsky, "Nuclear Receptor Minireview Series", J. Biol. Chem. 276(40), 36863-36864 (2001).
Pangborn, et al., "Safe and Convenient Procedure for Solvent Purification", Organometallics 15, 1518-1520 (1996).
Patent Cooperation Treaty, International Searching Authority, Search Report and Written Opinion for PCT/US2012/055186, 15 pages, dated May 7, 2013.
Sakaki, et al., "Synthesis and Structure-activity Relationship of Nocel RXR antagonists: orally active antidiabetic and antiobesity agents", Bioorg. Med. Chem. Lett. 17, 4804-4807 (2007).
Santin, et al., "Modulating Retinoid X Receptor with a Series of (E)-3-[4-Hydroxy-3-(3-alkoxy-5,5,8,8-tetramethyl-5,6,7,8-tetrahydronaphthalen-2-yl)phenyl]acrylic Acids and Their 4-Alkoxy Isomers", Journal of Medicinal Chemistry 52, 3150-3158 (2009).
Sherman, et al., "Central hypothyroidism associated with retinoid X receptor-selective ligands", N. Engl. J. Med. 340 (14), 1075-1079 (1999).
Simone, "Oncology: Introduction, Cecil Textbook of Medicine", 20th Edition, vol. 1, 1004-1010 (1996).
Svensson, et al., "Crystal structure of the heterodimeric complex of LXRa and RXRb ligand-binding domains in a fully agonistic conformation", EMBO J. 22(18), 4625-4633 (2003).
Thacher, et al., "Receptor Specificity of Retinoid-Induced Epidermal Hyperplasia: Effect of RXR-Selective Agonists and Correlation with Topical Irritation", Journal Pharmacology and Experimental Therapeutics 282(2), 528-534 (1997).
Thalesnano Nanotechnology Inc., "H-Cube Continuous-flow hydrogenation reactor", www.thalensnano.com/h-cube, published Apr. 9, 2006, Retrieved: Dec. 29, 2014.
Thompson, et al., "Distinct retinoid X receptor activation dunction-2 residues mediate transactivation in homodimeric and vitamin D receptor heterodimeric contexts", J. Mol. Endocrinol. 27(2), 211-227 (2001).
Vuligonda, et al., "Enantioselective Synthesis of Potent Retinoid X Receptor Ligands: Differential Biological Activities of Individual Antipodes", J. Med. Chem. 44, 2298-2303 (2001).
Wagner, et al., "Modeling, synthesis and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid (bexarotene)", Journal of Medicinal Chemistry, Oct. 2009, 52(19):5950-66.
Winum, et al., "Synthesis of New Targretin® Analogues that Induce Apoptosis in Leukemia HL-60 Cells", Bioorg. Med. Chem. Lett. 12: 3529-3532 (2002).
Yamauchi, et al., "Inhibition of RXR and PPARgamma ameliorate diet-induced obesity and type 2 diabetes", J. Clin. Invest. 108, 1001-1013 (2001).
Yen, et al., "A selective retinoid X receptor agonist bexarotene (Targretin) prevents and overcomes acquired paclitaxel (Taxol) resistance in human non-small cell lung cancer", Clinical Cancer Research, Dec. 2004, 10(24):8656-64.
Yen, et al., "Synergistic effect of a retinoid X receptor-selective ligand bexarotene (LGD1069, Targretin) and paclitaxel (Taxol) in mammary carcinoma", Breast Cancer Res. Treat. 88, 141-148 (2004).
Zimmerman, "Procedures used in the induction of mitotic recombination and mutation in the yeast *Saccharomyces cerevisiae*", Mutat Res 31, 71-86 (1975).

\* cited by examiner

THERAPEUTIC COMPOUNDS

CROSS-REFERENCE TO RELATED APPLICATIONS

This application is a Continuation of U.S. application Ser. No. 14/344,867, filed Mar. 13, 2014, which is a 35 U.S.C. 371 application of International Application No. PCT/US2012/055186, filed Sep. 13, 2012, which claims priority to U.S. Provisional Application No. 61/535,311, filed Sep. 15, 2011 and U.S. Provisional Application No. 61/681,519, filed Aug. 9, 2012, the contents of each of which are incorporated herein by reference in their entirety.

GOVERNMENT FUNDING

This invention was made with government support under 1R15CA139364-01A2 awarded by NIH/National Cancer Institute. The government has certain rights in the invention.

BACKGROUND OF THE INVENTION

The human retinoid X receptors (hRXRs) consist of three identified isoforms (α, β, γ) that function as transcription promoters often in partnership with other members of a larger nuclear receptor (NR) family of transcription regulators including the thyroid receptor (TR), the vitamin D receptor (VDR), the liver X receptor (LXR), the peroxisome proliferator-activated receptor (PPAR), and the retinoic acid receptor (RAR). While 9-cis-retinoic acid (9-cis-RA) and docosahexaenoic acid (DHA) have been shown to bind to hRXRs and promote RXR element (RXRE) regulated transcription (i.e. function as RXR agonists), it is still unclear if RXR has a bona fide endogenous molecular ligand. RXR has been described as the central NR regulator, because it often plays a critical role, either as a permissive or non-permissive partner, in heterodimer complexes that must be formed with the other NRs to regulate their respective response elements.

Recent studies have identified several RXR-selective-binding molecular ligands (rexinoids) that can modulate not only RXRE regulated transcription but also the heterodimer regulated transcription of other NRs. For instance, RXR is a subordinate partner in the RXR-RAR heterodimer, otherwise referred to as a non-permissive heterodimer, since transcription is not promoted in the RAR unliganded (apo-RAR) heterodimer with RXR. Additionally, the RXR-TR heterodimer is non-permissive. In contrast to these non-permissive heterodimers, permissive heterodimers such as RXR-PPAR allow transcription to be promoted in the presence of either RXR or PPAR agonists. The RXR-LXR heterodimer is also permissive. Hence, there is enormous potential for RXR agonists to activate or repress various biological pathways and effect therapeutic results for various conditions that would benefit from activation or repression of a specific pathway.

Six rexinoids described in the literature include Bexarotene (60), CD3254 (61), LGD100268 (62), a pyridyl-bexarotene analog (1), an unsaturated bexarotene analog (2), and the mono-fluorinated bexarotene analog (3).

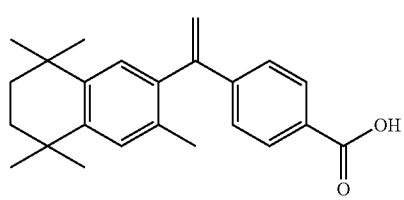

Bexarotene

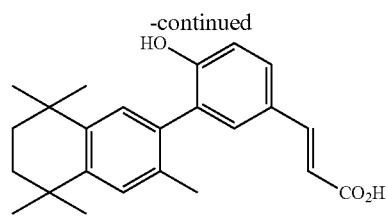

CD 3254

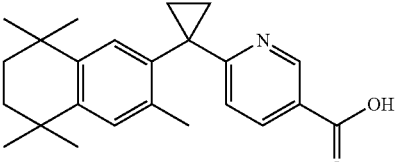

LGD100268

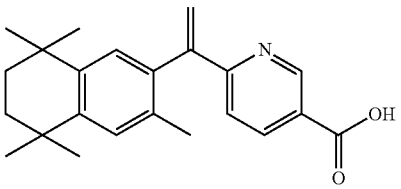

1

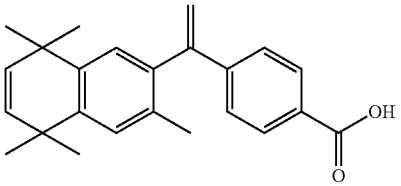

2

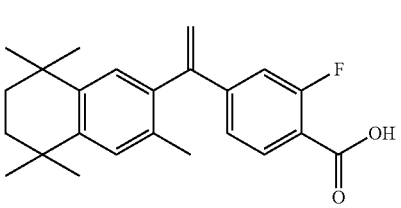

3

Bexarotene has been documented to have an $EC_{50}$ of 33, 24 and 25 nm for the RXR α, β, γ subtypes, respectively, and a $K_d$ of 14, 21, and 29 nm for the RXR α, β, γ subtypes, respectively, in a CV-1 cell line (Boehm, M. F., et al., "Synthesis and Structure-Activity Relationships of Novel Retinoid X Receptor-Selective Retinoids" *J. Med. Chem.* 1994, 37, 2930-2941). CD3254 appears to have an $EC_{50}$ on the order of 10 nm for the hRXRβ isoform (Santin, E. P., et al., "Modulating Retinoid X Receptor with a Series of (E)-3-[4-Hydroxy-3-(3-alkoxy-5,5,8,8-tetramethyl-5,6,7,8-tetrahydronaphthalen-2-yl)phenyl]acrylic Acids and Their 4-Alkoxy Isomers" *J. Med. Chem.* 2009, 52, 3150-3158). LGD100268 and 1 have been documented to have $EC_{50}$s of 4, 3, and 4 nm and 6, 9, and 5 nm for the RXR α, β, γ subtypes, respectively, and $K_d$s of 3, 3, and 3 nm and 22, 61, and 39 nm for the RXR α, γ, γ subtypes, respectively, in a CV-1 cell line (Boehm, M. F., et al., "Design and Synthesis of Potent Retinoid X Receptor Selective Ligands That Induce Apoptosis in Leukemia Cells" *J. Med. Chem.* 1995, 38, 3146-3155). While the unsaturated-bexarotene analog (2) has been reported, its ability to serve as an RXR agonist has not been published. Finally, the mono-fluorinated bexarotene analog (3) has an $EC_{50}$ of 43 nm and a $K_d$ of 12 nm in hRXR in Caco-2 cells (Wagner, C. E., et al., "Modeling, Synthesis and Biological Evaluation of Potential Retinoid X Receptor (RXR) Selective Agonists: Novel Analogues of 4-[1-(3,5,5,8,8-Pentamethyl-5,6,7,8-tetrahydro-2-naphthyl)ethynyl]benzoic Acid (Bexarotene)" *J. Med. Chem.* 2009, 52, 5950-5966).

Currently there is a need for additional chemical agents that are useful for treating or preventing cancer or treating or preventing Alzheimer's disease. There is also a need for anti-cancer or anti-Alzheimer's agents that have enhanced activity or that have improved pharmacologic properties such as increased solubility or better bioavailability.

SUMMARY OF THE INVENTION

In one embodiment the invention provides a compound of formula I:

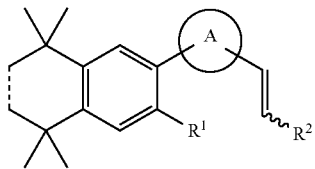

(I)

wherein:

$R^1$ is H, halo, hydroxy, cyano, nitro, ($C_1$-$C_6$)alkyl, ($C_3$-$C_6$)cycloalkyl, ($C_2$-$C_6$)alkenyl, ($C_1$-$C_6$)alkynyl, ($C_1$-$C_6$)alkoxycarbonyl, or ($C_1$-$C_6$)alkanoyloxy, wherein each ($C_1$-$C_6$)alkyl, ($C_3$-$C_6$)cycloalkyl, ($C_2$-$C_6$)alkenyl, ($C_1$-$C_6$)alkynyl, ($C_1$-$C_6$)alkoxycarbonyl, and ($C_1$-$C_6$)alkanoyloxy, is optionally substituted with one or more groups independently selected from halo, hydroxy, nitro, cyano, ($C_1$-$C_6$)alkoxy, and oxo (=O);

the bond represented by --- is a single bond or a double bond, ring A is a phenyl ring or a 6-membered heteroaryl ring, which phenyl ring or 6-membered heteroaryl ring is optionally substituted with one or more groups independently selected from halo, hydroxy, cyano, nitro, ($C_1$-$C_6$)alkyl, ($C_3$-$C_6$)cycloalkyl, ($C_2$-$C_6$)alkenyl, ($C_1$-$C_6$)alkynyl, ($C_1$-$C_6$)alkoxy, ($C_1$-$C_6$)alkoxycarbonyl, or ($C_1$-$C_6$)alkanoyloxy, wherein each ($C_1$-$C_6$)alkyl, ($C_3$-$C_6$)cycloalkyl, ($C_2$-$C_6$)alkenyl, ($C_1$-$C_6$)alkynyl, ($C_1$-$C_6$)alkoxy, ($C_1$-$C_6$)alkoxycarbonyl, and ($C_1$-$C_6$)alkanoyloxy, is optionally substituted with one or more groups independently selected from halo, hydroxy, nitro, cyano, and oxo (=O); and $R^2$ is COOH, B(OH)$_2$, or SO$_3$H;

or a salt thereof.

In one embodiment the invention provides a compound of formula II:

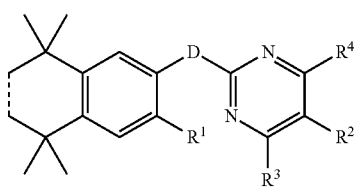

(II)

wherein:

$R^1$ is H, halo, hydroxy, cyano, nitro, ($C_1$-$C_6$)alkyl, ($C_3$-$C_6$)cycloalkyl, ($C_2$-$C_6$)alkenyl, ($C_1$-$C_6$)alkynyl, ($C_1$-$C_6$)alkoxy, ($C_1$-$C_6$)alkoxycarbonyl, or ($C_1$-$C_6$)alkanoyloxy, wherein each ($C_1$-$C_6$)alkyl, ($C_3$-$C_6$)cycloalkyl, ($C_2$-$C_6$)alkenyl, ($C_1$-$C_6$)alkynyl, ($C_1$-$C_6$)alkoxy, ($C_1$-$C_6$)alkoxycarbonyl, and ($C_1$-$C_6$)alkanoyloxy, is optionally substituted with one or more groups independently selected from halo, hydroxy, nitro, cyano, ($C_1$-$C_6$)alkoxy, and oxo (=O);

the bond represented by --- is a single bond or a double bond,

D is

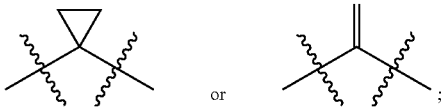

and at least one of one of $R^2$, $R^3$, and $R^4$ is COOH, B(OH)$_2$, or SO$_3$H; and the remaining $R^2$, $R^3$, and $R^4$ are each independently selected from H, COOH, B(OH)$_2$, SO$_3$H, halo, hydroxy, cyano, nitro, ($C_1$-$C_6$)alkyl, ($C_3$-$C_6$)cycloalkyl, ($C_2$-$C_6$)alkenyl, ($C_1$-$C_6$)alkynyl, ($C_1$-$C_6$)alkoxy, ($C_1$-$C_6$)alkoxycarbonyl, or ($C_1$-$C_6$)alkanoyloxy, wherein each ($C_1$-$C_6$)alkyl, ($C_3$-$C_6$)cycloalkyl, ($C_2$-$C_6$)alkenyl, ($C_1$-$C_6$)alkynyl, ($C_1$-$C_6$)alkoxy, ($C_1$-$C_6$)alkoxycarbonyl, and ($C_1$-$C_6$)alkanoyloxy, is optionally substituted with one or more groups independently selected from halo, hydroxy, nitro, cyano, ($C_1$-$C_6$)alkoxy, and oxo (=O);

or a salt thereof.

In one embodiment the invention provides a compound of formula III:

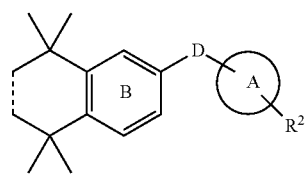

(III)

wherein:

ring B is substituted with at least one group independently selected from $R^a$, halo, hydroxy, cyano, nitro, ($C_2$-$C_6$)alkyl, ($C_3$-$C_6$)cycloalkyl, ($C_2$-$C_6$)alkenyl, ($C_1$-$C_6$)alkynyl, ($C_1$-$C_6$)alkoxy, ($C_1$-$C_6$)alkoxycarbonyl, or ($C_1$-$C_6$)alkanoyloxy, wherein each ($C_2$-$C_6$)alkyl, ($C_3$-$C_6$)cycloalkyl, ($C_2$-$C_6$)alkenyl, ($C_1$-$C_6$)alkynyl, ($C_1$-$C_6$)alkoxy, ($C_1$-$C_6$)alkoxycarbonyl, and ($C_1$-$C_6$)alkanoyloxy, is optionally substituted with one or more groups independently selected from halo, hydroxy, nitro, cyano, ($C_1$-$C_6$)alkoxy, and oxo (=O);

the bond represented by --- is a single bond or a double bond, ring A is a phenyl ring or a 6-membered heteroaryl ring, which phenyl ring or 6-membered heteroaryl ring is optionally substituted with one or more groups independently selected from halo, hydroxy, cyano, nitro, ($C_1$-$C_6$)alkyl, ($C_3$-$C_6$)cycloalkyl, ($C_2$-$C_6$)alkenyl, ($C_1$-$C_6$)alkynyl, ($C_1$-$C_6$)alkoxy, ($C_1$-$C_6$)alkoxycarbonyl, or ($C_1$-$C_6$)alkanoyloxy, wherein each ($C_1$-$C_6$)alkyl, ($C_3$-$C_6$)cycloalkyl, ($C_2$-$C_6$)alkenyl, ($C_1$-$C_6$)alkynyl, ($C_1$-$C_6$)alkoxy, ($C_1$-$C_6$)alkoxycarbonyl, and ($C_1$-$C_6$)alkanoyloxy, is optionally substituted with one or more groups independently selected from halo, hydroxy, nitro, cyano, and oxo (=O);

$R^2$ is COOH, B(OH)$_2$, or SO$_3$H;

D is

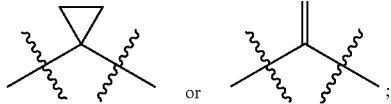

and $R^a$ is methyl that is substituted with hydroxy, nitro, cyano, ($C_1$-$C_6$)alkoxy, or oxo (=O), or methyl that is substituted with one or more halo;

or a salt thereof.

In one embodiment the invention provides a compound of formula IV:

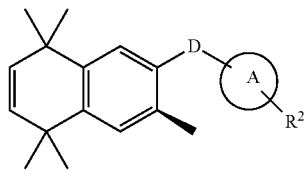

wherein:

ring A is a phenyl ring or a 6-membered heteroaryl ring, which phenyl ring or 6-membered heteroaryl ring is optionally substituted with one or more groups independently selected from halo, hydroxy, cyano, nitro, $(C_1-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, and oxo (=O);

$R^2$ is COOH, $B(OH)_2$, or $SO_3H$; and

D is

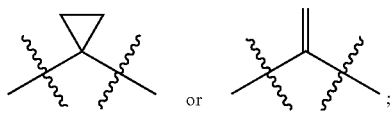

or a salt thereof.

In one embodiment the invention provides a compound as described in Examples 1-6 (i.e. 2-(1-(1,2,3,4-tetrahydro-1,1,4,4,6-pentamethylnaphthalen-7-yl)vinyl)pyrimidine-5-carboxylic acid, 2-[1-(3,5,5,8,8-pentamethyl-5,6,7,8-tetrahydronaphthalen-2-yl)cyclopropyl]pyrimidine-2-carboxylic acid, (E)-3-(3-(1,2,3,4-tetrahydro-1,1,4,4,6-pentamethylnaphthalen-7-yl)-4-methylphenyl)acrylic acid, (2E)-3-(3-(1,4-dihydro-1,1,4,4,6-pentamethylnaphthalen-7-yl)-4-methylphenyl)acrylic acid, (2E)-3-(3-(1,4-dihydro-1,1,4,4,6-pentamethylnaphthalen-7-yl)-4-hydroxyphenyl)acrylic acid, (E)-3-(4-(trifluoromethyl)-3-(1,2,3,4-tetrahydro-1,1,4,4,6-pentamethylnaphthalen-7-yl)phenyl)acrylic acid, or 2-fluoro-4-(1-(1,4-dihydro-1,1,4,4,6-pentamethylnaphthalen-7-yl)vinyl)benzoic acid, or a salt thereof.

The invention also provides a pharmaceutical composition comprising a compound of the invention, or a pharmaceutically acceptable salt thereof, in combination with a pharmaceutically acceptable diluent or carrier.

The invention also provides a method for inhibiting cancer cell (e.g., breast, lung, colon, pancreatic, skin, cutaneous T-cell lymphoma, acute promyelocytic leukemia, ovarian, bladder, kidney, and head and neck cancers, and Kaposi's sarcoma), growth comprising contacting the cell in vitro or in vivo with an effective amount of a compound of the invention, or a salt thereof. The off-label use of bexarotene, a known RXR agonist, and retinoids in other cancers is currently being researched.

The invention also provides a method for treating cancer (e.g., breast, lung, colon, pancreatic, skin, cutaneous T-cell lymphoma, acute promyelocytic leukemia, ovarian, bladder, kidney, and head and neck cancers, and Kaposi's sarcoma) in a mammal (e.g. a human) comprising administering to the mammal an effective amount of a compound of the invention, or a pharmaceutically acceptable salt.

The invention also provides a method for treating cancer (e.g., breast, lung, colon, pancreatic, skin, cutaneous T-cell lymphoma, acute promyelocytic leukemia, ovarian, bladder, kidney, and head and neck cancers, and Kaposi's sarcoma) in a mammal (e.g. a human) in need of such treatment comprising administering to the mammal an effective amount of a compound of the invention, or a pharmaceutically acceptable salt.

The invention also provides a method for treating cancer (e.g., breast, lung, colon, pancreatic, skin, cutaneous T-cell lymphoma, acute promyelocytic leukemia, ovarian, bladder, kidney, and head and neck cancers, and Kaposi's sarcoma) in a mammal (e.g. a human) diagnosed with cancer comprising administering to the mammal an effective amount of a compound of the invention, or a pharmaceutically acceptable salt.

The invention also provides a method for activating RXR in a cell comprising contacting the cell in vitro or in vivo with an effective amount of a compound of the invention, or a salt thereof.

The invention also provides a compound of the invention, or a pharmaceutically acceptable salt thereof, for use in medical therapy.

The invention also provides a compound of the invention, or a pharmaceutically acceptable salt thereof, for the manufacture of a medicament useful for the treatment of cancer (e.g., breast, lung, colon, pancreatic, skin, cutaneous T-cell lymphoma, acute promyelocytic leukemia, ovarian, bladder, kidney, and head and neck cancers, and Kaposi's sarcoma) in a mammal (e.g. a human).

The invention also provides a compound of the invention, or a pharmaceutically acceptable salt thereof, for use in the prophylactic or therapeutic treatment of cancer (e.g., breast, lung, colon, pancreatic, skin, cutaneous T-cell lymphoma, acute promyelocytic leukemia, ovarian, bladder, kidney, and head and neck cancers, and Kaposi's sarcoma) in a mammal.

The invention also provides a method for treating Alzheimer's disease in a human comprising administering to the human an effective amount of compound of the invention, or a pharmaceutically acceptable salt.

The invention also provides a method for treating Alzheimer's disease in a human in need of such treatment comprising administering to the human an effective amount of compound of the invention, or a pharmaceutically acceptable salt.

The invention also provides a method for treating Alzheimer's disease in a human diagnosed with Alzheimer's disease comprising administering to the human an effective amount of compound of the invention, or a pharmaceutically acceptable salt.

The invention also provides a compound of the invention, or a pharmaceutically acceptable salt thereof, for the manufacture of a medicament useful for the treatment of Alzheimer's disease in a human.

The invention also provides a compound of the invention, or a pharmaceutically acceptable salt thereof, for use in the prophylactic or therapeutic treatment of Alzheimer's disease in a human.

The invention also provides processes and novel intermediates that are useful for preparing the compounds of the invention.

DETAILED DESCRIPTION

Figure 1:
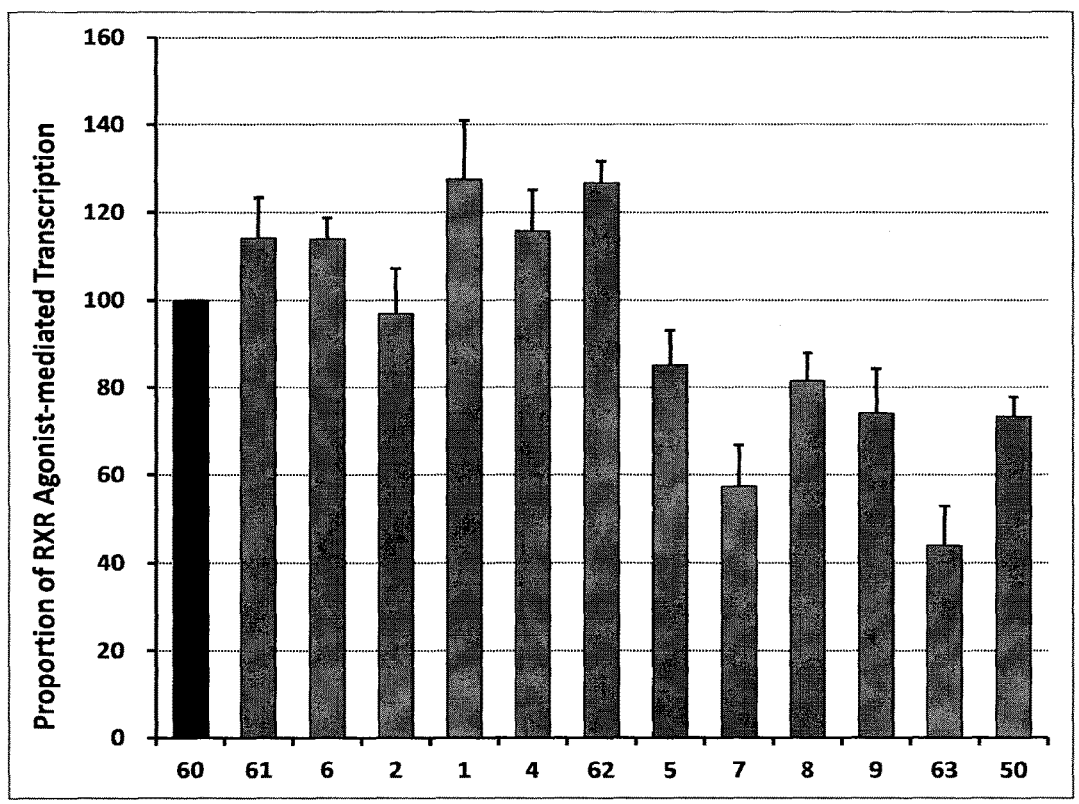
FIG. 1 illustrates the recognition of potential RXR selective agonists via a mammalian two-hybrid assay in human colon cancer cells, HCT-116. The cell line was transfected with pCMVhRXR binding domain vector (BD), hRXR activation domain (AD), pFR-Luc reporter gene containing BD-binding sites, and a renilla control plasmid. Cells were transfected for 7 hours utilizing a liposome-mediated transfection protocol then exposed to either the ethanol vehicle or $10^{-7}$ M Bexarotene or the indicted analog. After 24 hours the cells were lysed and a luciferase assay was completed. Analog dependent RXR binding and homodimerization, as measured by luciferase output, was compared to the parent compound Bexarotene.

The term "activating", such as used in the phrase "activating RXR", means to promote transcriptional activity.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "6-membered heteroaryl ring" includes rings with at least two carbon atoms and 1, 2, 3, or 4 heteroatoms.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkanoyloxy can be formyloxy, acetoxy, propanoyloxy, butanoyloxy, isobutanoyloxy, pentanoyloxy, or hexanoyloxy; aryl can be phenyl, indenyl, or naphthyl; and heteroaryl can be pyrazinyl, pyridazine, triazine, pyridyl, or pyrimidinyl, or an N-oxide thereof.

In one embodiment of the invention the compound of formula I is not:

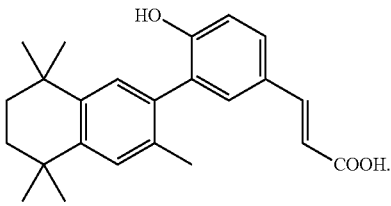

In one embodiment of the invention the compound of formula I is not:

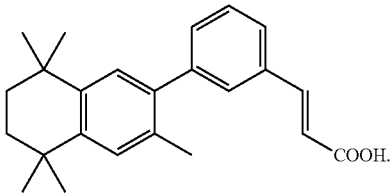

In one embodiment of the invention ring A is a phenyl ring substituted with one or more groups independently selected from halo, cyano, nitro, $(C_1-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, and oxo (=O).

In one embodiment of the invention ring A is a 6-membered heteroaryl ring, which is optionally substituted with one or more groups independently selected from halo, hydroxy, cyano, nitro, $(C_1-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, and oxo (=O).

In one embodiment of the invention $R^1$ is H, halo, hydroxy, cyano, nitro, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O).

In one embodiment of the invention $R^1$ is halo, hydroxy, cyano, nitro, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O).

In one embodiment of the invention the bond represented by --- is a single bond.

In one embodiment of the invention the bond represented by --- is a double bond.

In one embodiment of the invention D is

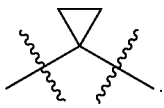 [SMILES: *C1(*)CC1]

In one embodiment of the invention D is

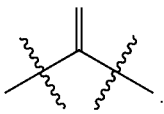 [SMILES: *C(*)=C]

In one embodiment of the invention one of $R^2$, $R^3$, and $R^4$ is COOH.

In one embodiment of the invention one of $R^2$, $R^3$, and $R^4$ is $SO_3H$.

In one embodiment of the invention at least one of one of $R^2$, $R^3$, and $R^4$ is COOH or $SO_3H$; and the remaining $R^2$, $R^3$, and $R^4$ are each independently selected from COOH, $SO_3H$, halo, hydroxy, cyano, nitro, $(C_1-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O).

In one embodiment the invention provides the compound:

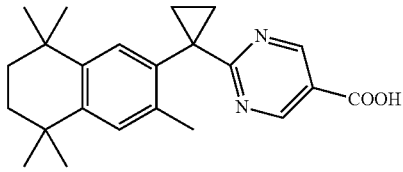 [SMILES: Cc1cc2c(cc1C1(c3ncc(C(=O)O)cn3)CC1)C(C)(C)CCC2(C)C]

or a salt thereof.

In one embodiment of the invention the compound of formula III is not:

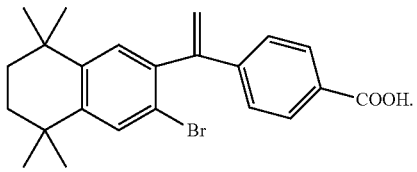 [SMILES: C=C(c1ccc(C(=O)O)cc1)c1cc2c(cc1Br)C(C)(C)CCC2(C)C]

In one embodiment of the invention ring B is substituted with at least one group independently selected from $R^a$, fluoro, chloro, iodo, hydroxy, cyano, nitro, $(C_2-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, or $(C_1-C_6)$alkanoyloxy, wherein each $(C_2-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O).

In one embodiment of the invention ring B is substituted with at least one group independently selected from $R^a$, hydroxy, cyano, nitro, $(C_2-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, or $(C_1-C_6)$alkanoyloxy, wherein each $(C_2-C_6)$alkyl, $(C_3-C_6)$cycloalkyl, $(C_2-C_6)$alkenyl, $(C_1-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O).

In one embodiment of the invention $R^2$ is COOH.

In one embodiment of the invention $R^2$ is $SO_3H$.

In one embodiment of the invention the compound of formula IV is not:

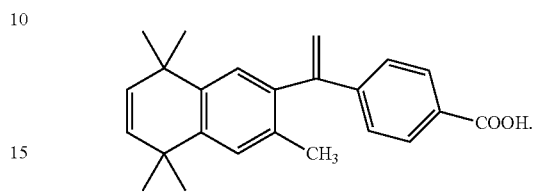

In one embodiment of the invention the compound of formula IV is not:

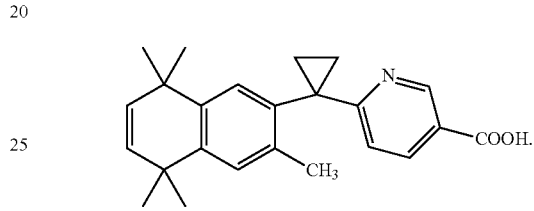

In one embodiment the invention provides a compound selected from:
2-(1-(1,2,3,4-tetrahydro-1,1,4,4,6-pentamethylnaphthalen-7-yl)vinyl)pyrimidine-5-carboxylic acid,
2-[1-(3,5,5,8,8-pentamethyl-5,6,7,8-tetrahydronaphthalen-2-yl)cyclopropyl]pyrimidine-2-carboxylic acid,
(E)-3-(3-(1,2,3,4-tetrahydro-1,1,4,4,6-pentamethylnaphthalen-7-yl)-4-methylphenyl)acrylic acid,
(2E)-3-(3-(1,4-dihydro-1,1,4,4,6-pentamethylnaphthalen-7-yl)-4-methylphenyl)acrylic acid,
(2E)-3-(3-(1,4-dihydro-1,1,4,4,6-pentamethylnaphthalen-7-yl)-4-hydroxyphenyl)acrylic acid,
(E)-3-(4-(trifluoromethyl)-3-(1,2,3,4-tetrahydro-1,1,4,4,6-pentamethylnaphthalen-7-yl)phenyl)acrylic acid,
2-fluoro-4-(1-(1,4-dihydro-1,1,4,4,6-pentamethylnaphthalen-7-yl)vinyl)benzoic acid,
(E)-3-(5-(1,2,3,4-tetrahydro-1,1,4,4,6-pentamethylnaphthalen-7-yl)-6-methylpyridin-3-yl)acrylic acid, and
(E)-3-(4-(1,2,3,4-tetrahydro-1,1,4,4,6-pentamethylnaphthalen-7-yl)-5-methylpyridin-2-yl)acrylic acid,
and salts thereof.

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949. Compounds that are non-toxic and non-mutagenic at typical dose levels will have useful doses. (Mortelmans, K.; Zeiger, E. "The Ames Salmonella/microsome mutagenicity assay." Mutat. Res. 2000, 455, 29-60.)

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form. In certain embodiments, the dose is about 300 mg/m$^2$/day.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents. In certain embodiments, compounds of the invention can be administered in combination with agents that are useful for the treatment of breast cancer. (Yen, W. et al. "Synergistic effect of a retinoid X receptor-selective ligand bexarotene (LGD1069, Targretin) and paclitaxel (Taxol) in mammary carcinoma" Breast Cancer Research and Treatment, 2004, 88, 141-148.) In certain embodiments, compounds of the invention can be administered in combination with agents that are useful for the treatment of lung cancer. (Yen, W.-C.; Corpuz, M. R.; Prudente, R. Y.; Cooke, T. A.; Bissonnette, R. P.; Negro-Vilar, A.; Lamph, W. W. "A Selective Retinoid X Receptor Agonist Bexarotene (Targretin) Prevents and Overcomes Acquired Paclitaxel (Taxol) Resistance in Human Non-Small Cell Lung Cancer." Clin. Cancer Res. 2004, 10, 8656-8664.). In certain embodiments, compounds of the invention can be administered in combination with agents that are useful for the treatment of diabetes. (Mukherjee, R.; Davies, P. J. A.; Crombie, D. L.; Bischoff, E. D.; Cesario, R. M.; Jow, L.; Hamanns, L. G.; Boehm, M. F.; Mondon, C. E.; Nadzan, A. M.; Paterniti, J. R.; Heyman, R. A. "Sensitization of diabetic and obese mice to insulin by retinoid X receptor agonists." Nature 1997, 386, 407-410.) Accordingly, in one embodiment the invention also provides a composition comprising a compound of the invention, or a pharmaceutically acceptable salt thereof, at least one other therapeutic agent, and a pharmaceutically acceptable diluent or carrier. The invention also provides a kit comprising a compound of the invention, or a pharmaceutically acceptable salt thereof, at least one other therapeutic agent, packaging material, and instructions for administering the compound of the invention or the pharmaceutically acceptable salt thereof and the other therapeutic agent or agents to an animal to treat cancer or diabetes.

The ability of a compound of the invention to act as an RXR agonist (e.g. to promote or activate RXR, i.e., promote or activate RXR regulated gene expression) may be determined using pharmacological models which are well known to the art, or using Test A or Test B described below.

Test A. RXR Selective Agonist Assay (Mammalian Two-hybrid Assay).

Compounds were tested for RXR selective agonist activity via a mammalian two-hybrid assay in human colon cancer cells, HCT-116. The cell line was transfected with pCMVhRXR binding domain vector (BD), hRXR activation domain (AD), pFR-Luc reporter gene containing BD-binding sites, and a renilla control plasmid. Cells were transfected for 7 hours utilizing a liposome-mediated transfection protocol then exposed to either the ethanol vehicle or $10^{-7}$ M Bexarotene or the indicted analog. After 24 hours the cells were lysed and a luciferase assay was completed. Analog dependent RXR binding and homodimerization, as measured by luciferase output, was compared to the parent compound Bexarotene.

Experimental results from Test A for representative compounds of the invention are shown in FIG. 1. These results demonstrate that compounds of the invention are RXR agonists. Accordingly, compounds of the invention may be useful as therapeutic agents for the treatment of cancer or Alzheimer's disease. Such cancers include but are not limited to, colon, breast, lung, pancreatic, skin, cutaneous T-cell lymphoma, acute promyelocytic leukemia, ovarian, bladder, kidney, and head and neck cancers, and Kaposi's sarcoma. Additionally, compounds of the invention may be useful as pharmacological tools for the further investigation of RXR function.

Test B. RXR Agonist Assay (RXRE-luciferase Based Assay).

Compounds were tested for RXR agonist activity via an RXRE-luciferase based system utilizing human colon cancer cells HCT-116. The cell line was transfected with hRXRα, an RXRE luciferase reporter gene, renilla control plasmid, and carrier DNA (pTZ18U). Cells were transfected for 7 hours utilizing a liposome-mediated transfection protocol then exposed to either the ethanol vehicle or $10^{-7}$ M Bexarotene or the indicted analog. After 24 hours the cells were lysed and a luciferase assay was completed. Analog dependent, RXR-mediated transcription, as measured by luciferase output, was compared to the parent compound Bexarotene.

Figure 2:
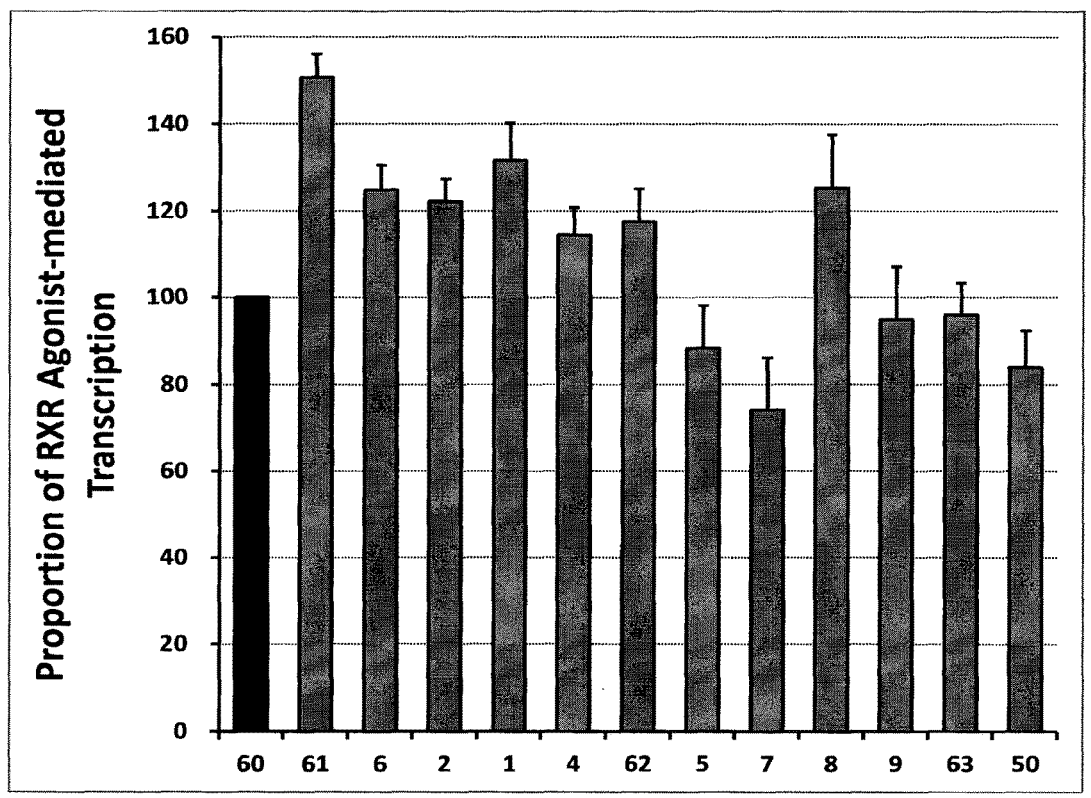
FIG. 2 illustrates the detection of potential RXR agonists via an RXRE-luciferase based system utilizing human colon cancer cells, HCT-116. The cell line was transfected with hRXRα, an RXRE luciferase reporter gene, renilla control plasmid, and carrier DNA (pTZ18U). Cells were transfected for 7 hours utilizing a liposome-mediated transfection protocol then exposed to either the ethanol vehicle or $10^{-7}$ M Bexarotene or the indicted analog. After 24 hours the cells were lysed and a luciferase assay was completed. Analog dependent, RXR-mediated transcription, as measured by luciferase output, was compared to the parent compound Bexarotene.

Experimental results from Test B for representative compounds of the invention are shown in FIG. 2. These results demonstrate that compounds of the invention are RXR agonists. Accordingly compounds of the invention may be useful as therapeutic agents for the treatment of cancer or Alzheimer's disease. Such cancers include but are not limited to, breast, lung, colon, pancreatic, skin, cutaneous T-cell lymphoma, acute promyelocytic leukemia, ovarian, bladder, kidney, and head and neck cancers, and Kaposi's sarcoma. Additionally, compounds of the invention may be useful as pharmacological tools for the further investigation of RXR function.

A variety of literature compounds were prepared following published procedures or the methods described herein below.

Preparation of Compound 1 and LGD100268.

Scheme 1

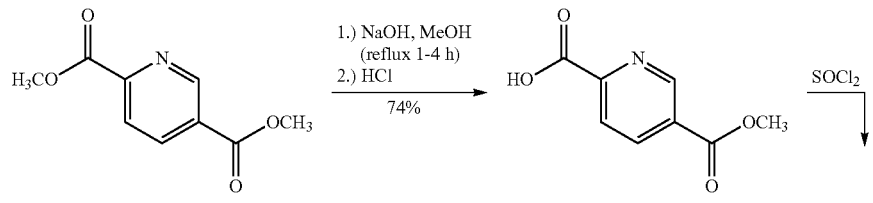

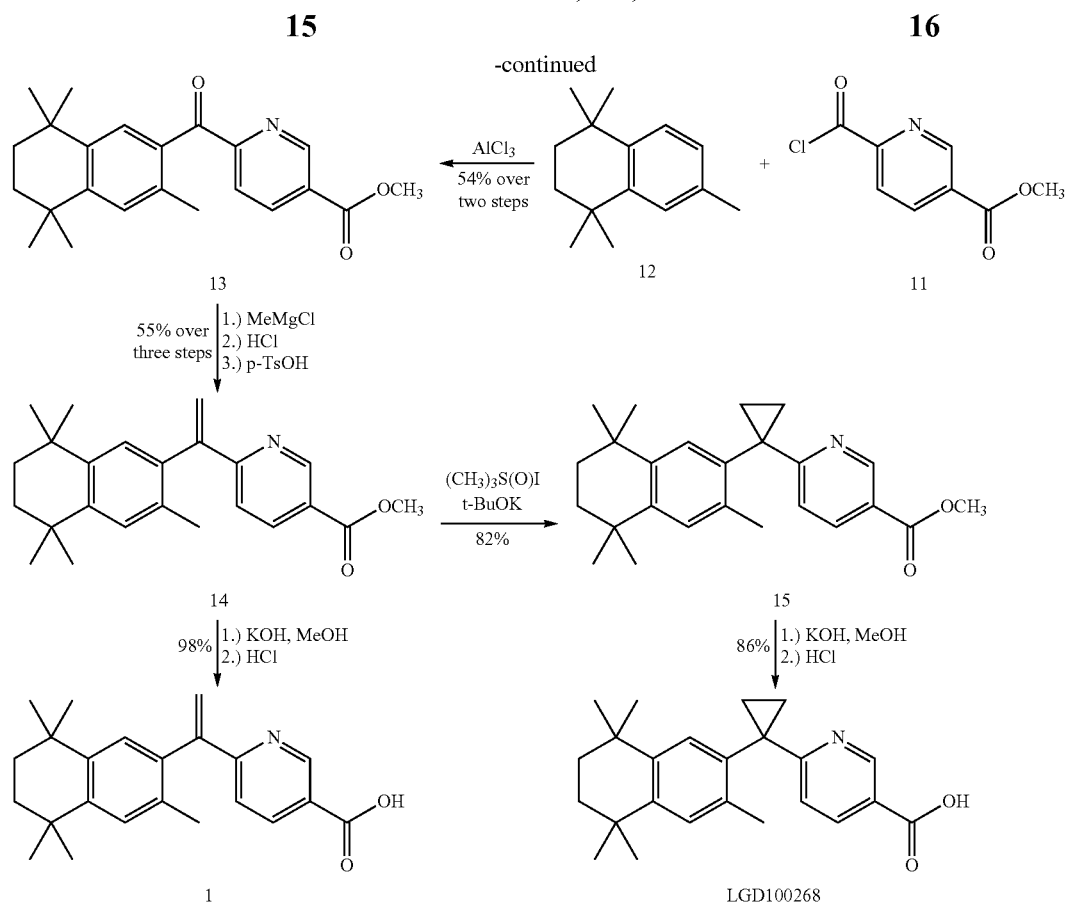

5-(methoxycarbonyl)pyridine-2-carboxylic acid (10). The protocol of Faul et al. was followed (Faul, M. M., et al., "Synthesis of Novel Retinoid X Receptor-Selective Retinoids" J. Org. Chem. 2001, 66, 5772-5782). To a suspension of dimethyl pydrine-2,5-dicarboxylate (10.09 g, 51.7 mmol) in methanol (130 mL) was added sodium hydroxide pellets (2.20 g, 55.0 mmol), and the heterogeneous reaction was stirred and refluxed for 4 h. After cooling to 65° C., 2.0 N HCl (38 mL, 76 mmol) was slowly added, and over the course of addition, the solid dissolved and a precipitate formed. The reaction solution was allowed to cool to room temperature, and then it was cooled in an ice-bath and filtered. The filter-cake was washed with water to give an off-white product (7.71 g, 82%). A sample of this crude, filtered product (1.09 g) was dissolved in boiling water (70 mL), and the solution was slowly cooled to room temperature, and then cooled in an ice-bath, before it was filtered to give a white, crystalline powder (0.98 g) at a 74% overall yield: $^1$H NMR (400 MHz, d6-DMSO) δ 9.15 (dd, J=2.0, 0.8, 1H), 8.44 (dd, J=8.0, 2.0, 1H), 8.15 (dd, J=8.0, 0.8, 1H), 3.91 (s, 3H), 3.34 (br s, 1H); $^{13}$C NMR (100.6 MHz, d6-DMSO) δ 165.5, 164.6, 151.7, 149.8, 138.3, 127.9, 124.6; LC-FAB-MS (M+H)+ calcd for $C_8H_8NO_4$ 182.0453, found 182.0458.

Methyl 6-[(3,5,5,8,8-Pentamethyl-5,6,7,8-tetrahydronaphthalen-2-yl)carbonyl]nicotinate (13). The procedure of Faul et al. was followed. Methyl 6-(chlorocarbonyl)-pyridine-3-carboxylate (11) was synthesized by refluxing 5-(methoxycarbonyl)pyridine-2-carboxylic acid (10) (1.20 g, 6.62 mmol) in thionyl chloride (12.0 mL, 165 mmol) in a 100 mL one-neck round bottom flask fitted with a water-cooled reflux condenser. Excess thionyl chloride was removed in vacuo to give crude 11 as an off-white solid, and this solid was dissolved in dry benzene (ca. 20 mL) and evaporated to dryness to remove residual thionyl chloride. The acid chloride 11 was dried on high vacuum to remove residual benzene. To a 2-neck, 50 mL round bottom flask equipped with a reflux condenser and magnetic stir-bar was added 12 (1.40 g, 6.91 mmol) followed by a solution of crude acid chloride 11 (6.62 mmol) in DCM (15 mL). Aluminum chloride (2.20 g, 16.5 mmol) was added to the reaction solution at room temperature slowly, with stirring, and the reaction solution turned from colorless to red accompanied by the evolution of gas and heat. The reaction was stirred for 5 min then heated to reflux for 15 min. The reaction was judged to be complete by TLC, and the solution was poured into an ice solution (25 mL) acidified with a 20% HCl solution (8 mL) and ethyl acetate was added (13 mL). The aqueous and organic layers were separated, and the aqueous layer was extracted with ethyl acetate (15 mL, twice). The combined organics were washed with water and brine, dried over sodium sulfate, filtered and concentrated to give crude 13. Crude 13 was purified by column chromatography (250 mL SiO$_2$, hexanes:ethyl acetate 95:5 to 85:15) to give 13 (1.30 g, 54%) as an off-white, crystalline solid: $^1$H NMR (400 MHz, CDCl$_3$) δ 9.26 (dd, J=2.0, 0.8, 1H), 8.49 (dd, J=8.0, 2.0, 1H), 8.10 (dd, J=8.0, 0.8, 1H), 7.42 (s, 1H), 7.21 (s, 1H), 3.99 (s, 3H), 2.39 (s, 3H), 1.68 (s, 4H), 1.29 (s, 6H), 1.20 (s, 6H); $^{13}$C NMR (100.6 MHz, CDCl$_3$) δ 195.8, 165.1, 158.6, 149.9, 149.2, 141.6, 138.1, 135.7, 133.2, 130.3, 129.7, 127.5, 123.8, 52.7, 34.8, 34.8, 34.4, 33.8, 31.6, 31.5, 20.5; LC-MS (M+H)+ calcd for $C_{23}H_{28}NO_3$ 366.2069, found 366.2070.

Methyl 6-[(3,5,5,8,8-Pentamethyl-5,6,7,8-tetrahydronaphthalen-2-yl)ethenyl]nicotinate (14). The procedure of Faul et al. was followed. To a 100 mL round bottom flask charged with 13 (1.0077 g, 2.757 mmol) was added toluene (10 mL) and the solution was cooled in a salt-water ice bath to −15° C. with stirring, under nitrogen. To this solution was added a 22 wt % solution of MeMgCl in THF (1.20 mL, 3.60 mmol), and the reaction was stirred for 15 min at −15° C. and then warmed to room temperature and stirred for 35 min before quenching with 1N HCl (7 mL, 7 mmol). The reaction mixture was then separated and the aqueous layer was extracted with ethyl acetate. The combined organic layers were dried over sodium sulfate, filtered and concentrated to give a crude alcohol intermediate that was used without further purification. To this crude intermediate in a 100 mL round bottom flask was added p-toluenesulfonic acid monohydrate (0.5247 g, 2.76 mmol) and toluene (40 mL), and the reaction was refluxed for 3 h into a Dean-Stark apparatus half-filled with toluene (6 mL). After the reaction had cooled to room temperature, it was added to a solution of sodium carbonate (0.78 g) in water (15 mL), shaken vigorously, and the layers were separated. The aqueous layer was extracted with ethyl acetate, and the combined organic layers were washed with brine, dried over sodium sulfate, filtered and concentrated in vacuo, to give a crude brown product that was purified by column chromatography (150 mL $SiO_2$, hexanes:ethyl acetate 97.5:2.5 to 95:5) to give 14 (0.5595 g, 55%) as a white, fiber-like solid: $^1$H NMR (400 MHz, $CDCl_3$) δ 9.22 (dd, J=2.0, 0.8, 1H), 8.15 (dd, J=8.0, 2.0, 1H), 7.14 (s, 1H), 7.11 (s, 1H), 7.02 (dd, J=8.4, 0.8, 1H), 6.54 (d, J=2.0, 1H), 5.51 (d, J=2.0, 1H), 3.94 (s, 3H), 1.98 (s, 3H), 1.69 (s, 4H), 1.31 (s, 6H), 1.26 (s, 6H); $^{13}$C NMR (100.6 MHz, $CDCl_3$) δ 165.8, 161.1, 150.6, 148.0, 144.5, 142.5, 137.6, 136.7, 132.7, 128.0, 124.1, 121.1, 121.0, 52.2, 35.1, 35.0, 33.9, 33.8, 31.9, 31.8, 19.8; LC-MS (M+H)+ calcd for $C_{24}H_{30}NO_2$ 364.2277, found 364.2272.

Methyl 6-[(3,5,8,8-Pentamethyl-5.6,7,8-tetrahydronaphthalen-2-yl)cyclopropyl]nicotinate (15). Again, the procedure of Faul et al. was followed. To a suspension of trimethylsulfoxonium iodide (0.365 g, 1.66 mmol) in DMSO (1.2 mL) was added a 20 wt % solution of potassium tert-butoxide in THF (0.94 mL, 1.67 mmol). A solution of 14 (0.40 g, 1.10 mmol) in THF (4.8 mL) was added dropwise over 20 min at 30-34° C. with stirring. The reaction was stirred for 60 min at 35° C., then cooled to room temperature and quenched with 1N HCl (5 mL). The layers were separated and the aqueous layer was extracted with ethyl acetate. The combined organic layers were washed with brine, dried over sodium sulfate, and concentrated to give an off-white crude solid that was purified by column chromatography (150 mL $SiO_2$, hexanes:ethyl acetate 97.5:2.5 to 90:10) to give 15 (0.3411 g, 82%) as a white crystalline solid: $^1$H NMR (400 MHz, $CDCl_3$) δ 9.08 (dd, J=2.4, 0.8, 1H), 7.98 (dd, J=8.4, 2.4, 1H), 7.27 (s, 1H), 7.11 (s, 1H), 6.74 (dd, J=8.4, 0.8, 1H), 3.90 (s, 3H), 2.11 (s, 3H), 1.82-1.83 (m, 2H), 1.69 (s, 4H), 1.35-1.36 (m, 2H), 1.30 (s, 6H), 1.27 (s, 6H); $^{13}$C NMR (100.6 MHz, $CDCl_3$) δ 169.2, 166.1, 150.4, 143.8, 142.6, 137.1, 136.5, 135.7, 129.2, 128.3, 122.1, 120.7, 52.0, 35.1, 34.0, 33.9, 31.9, 31.8, 30.3, 20.2, 19.2; LC-MS (M+H)+ calcd for $C_{25}H_{32}NO_2$ 378.2433, found 378.2422.

Methyl 6-(1-(1,2,3,4-tetrahydro-1,1,4,4,6-pentamethylnaphthalen-7-yl)vinyl)pyridine-3-carboxylate (1). To a suspension of 14 (0.2898 g, 0.797 mmol) in methanol (5.0 mL) was added a solution of KOH (0.116 g) in water (0.18 mL), and the reaction was refluxed at 85° C. for 1 h. The reaction solution was cooled to room temperature and quenched with 20% HCl (26 mL). The crude precipitate was filtered and dried to give a crude white product (0.2753 g, 98%) that was recrystallized from hexanes:ethyl acetate 4:1 to give the pure 1 as a white crystalline solid: $^1$H NMR (400 MHz, $CDCl_3$) δ 13.51 (br s, 1H), 9.47 (s, 1H), 8.82 (dd, J=8.4, 2.0, 1H), 7.41 (d, J=8.4, 1H), 7.23 (s, 1H), 7.15 (s, 1H), 7.10 (s, 1H), 6.08 (s, 1H), 2.01 (s, 3H), 1.68 (s, 4H), 1.29 (s, 6H), 1.24 (s, 6H); $^{13}$C NMR (100.6 MHz, $CDCl_3$) δ 161.8, 154.3, 146.4, 146.3, 143.6, 139.9, 133.0, 132.5, 130.0, 128.8, 128.6, 128.1, 125.6, 34.8, 34.1, 33.9, 31.8, 31.7, 19.7; LC-MS (M+H)+ calcd for $C_{23}H_{28}NO_2$ 350.2120, found 350.2111. Anal. Calcd for $C_{24}H_{29}NO_2 \cdot HCl$: C, 71.58; H, 7.31; N, 3.63. Found: C, 72.64; H, 7.35; N, 3.62.

6-[1-(3,5,5,8,8-Pentamethyl-5,6,7,8-tetrahydronaphthalen-2-yl)cyclopropyl]nicotinic Acid (LGD100268). To a suspension of 15 (0.3043 g, 0.806 mmol) in methanol (8.0 mL) was added a solution of KOH (0.1287 g) in water (0.18 mL), and the reaction was refluxed at 85° C. for 1 h. The reaction solution was cooled to room temperature and quenched with 20% HCl (27 mL). The crude precipitate was filtered and dried to give a crude white product (0.2543 g, 86%) that was recrystallized from hexanes:ethyl acetate 4:1 to give the pure LGD100268 as a white crystalline solid (0.147 g, 50%): $^1$H NMR (400 MHz, $CDCl_3$) δ 11.69 (br s, 1H), 9.18 (dd, J=2.0, 0.8, 1H), 8.05 (dd, J=8.4, 2.0, 1H), 7.27 (s, 1H), 7.12 (s, 1H), 6.79 (dd, J=8.4, 0.8, 1H), 2.13 (s, 3H), 1.86-1.87 (m, 2H), 1.69 (s, 4H), 1.39-1.40 (m, 2H), 1.31 (s, 6H), 1.27 (s, 6H); $^{13}$C NMR (100.6 MHz, $CDCl_3$) δ 170.8, 170.2, 151.0, 143.9, 142.7, 137.2, 136.9, 135.7, 129.2, 128.3, 121.4, 120.9, 35.1, 34.0, 33.9, 31.9, 31.8, 30.5, 20.5, 19.2; LC-MS (M+H)+ calcd for $C_{24}H_{30}NO_2$ 364.2277, found 364.2265. Anal. Calcd for $C_{24}H_{29}NO_2$: C, 79.30; H, 8.04; N, 3.85. Found: C, 78.76; H, 7.93; N, 3.76.

Preparation of Compound 2.

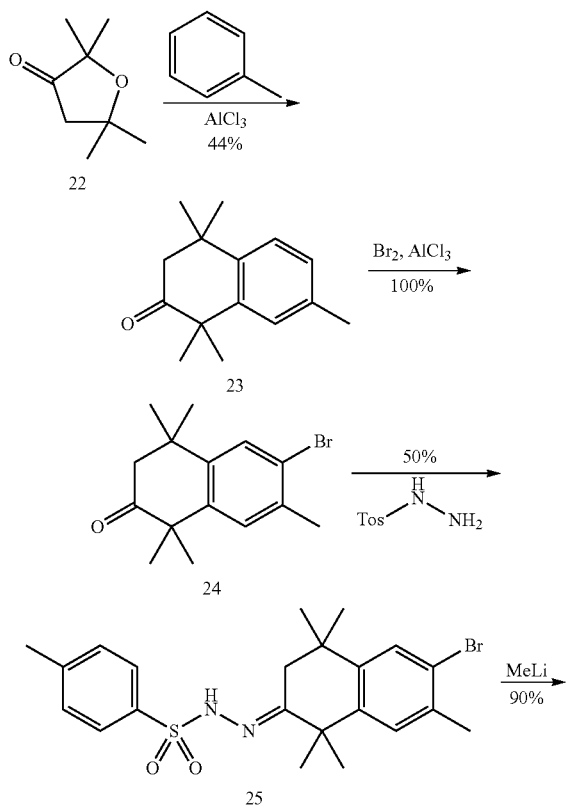

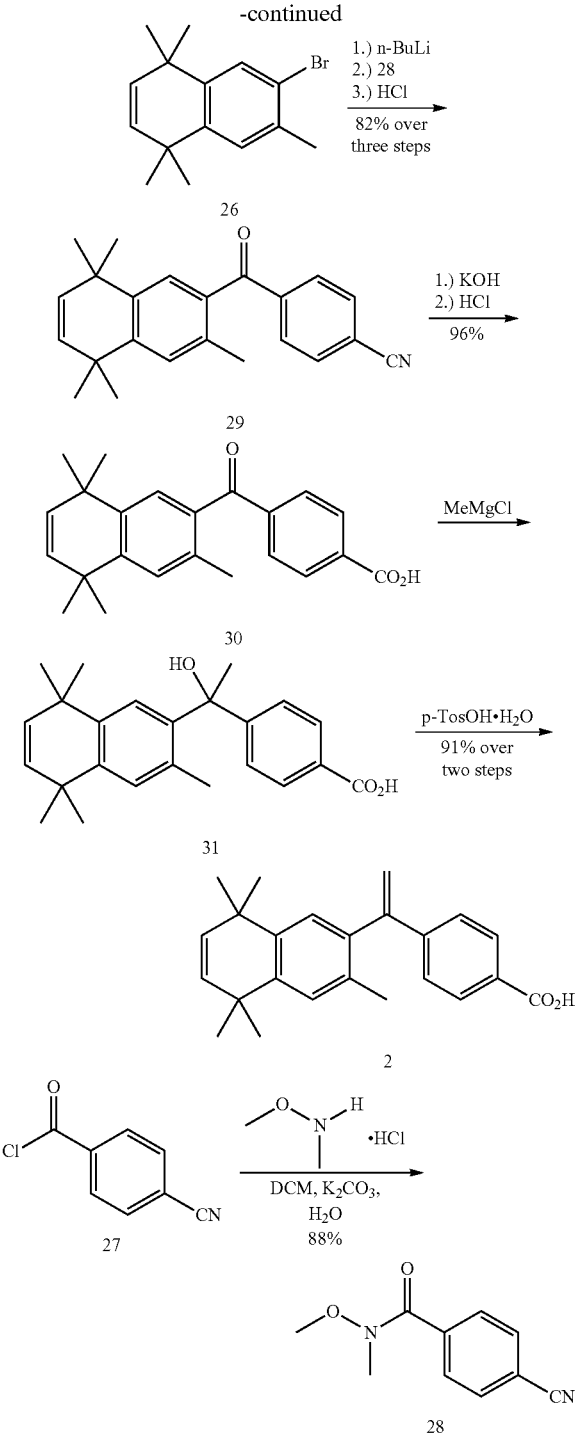

warmed to room temperature and stirred for 2 h, and then heated to 50-55° C. with stirring for 15 min. The reaction was cooled to room temperature, and then poured onto ice water (50 mL) and extracted with ethyl acetate. The combined organic layers were washed with brine, dried over sodium sulfate, filtered and concentrated in vacuo. The resulting crude solid was purified by column chromatography (150 mL SiO$_2$, hexanes:ethyl acetate 98:2) to give 23 (1.6348 g, 44%) as a white crystalline solid: $^1$H NMR (400 MHz, CDCl$_3$) δ 7.26 (d, J=8.0, 1H), 7.13 (s, 1H), 7.05 (d, J=8.0, 1H), 2.63 (s, 2H), 2.35 (s, 3H), 1.44 (s, 6H), 1.31 (s, 6H); $^{13}$C NMR (100.6 MHz, CDCl$_3$) δ 214.5, 142.9, 140.6, 136.3, 127.7, 127.4, 124.3, 51.5, 47.9, 37.6, 30.6, 28.4, 21.0; GC-MS (M)+ calcd for C$_{15}$H$_{20}$O 216.1514, found 216.1523.

6-Bromo-3,4-dihydro-1,1,4,4,7-pentamethylnaphthalen-2(1H)-one (24). A DCM (22.0 mL) solution of 23 (3.193 g, 14.76 mmol) at 0° C. was stirred during the addition of aluminum chloride (3.993 g, 29.95 mmol), and the mixture was stirred at 0° C. for 5 min. To this solution was added a solution of bromine (0.90 mL, 17.47 mmol) in DCM (11.0 mL) dropwise, and the reaction solution was stirred for 30 min at 0° C. The reaction solution was poured onto ice (50 mL) and extracted with ethyl acetate. The combined organic layers were washed with brine, dried over sodium sulfate, and concentrated in vacuo to give a crude product that was purified by column chromatography (150 mL SiO$_2$, hexanes: ethyl acetate 98:2) to give 24 (4.36 g, 100%) as a white crystalline solid: $^1$H NMR (400 MHz, CDCl$_3$) δ 7.50 (s, 1H), 7.15 (s, 1H), 2.60 (s, 2H), 2.38 (s, 3H), 1.42 (s, 6H), 1.28 (s, 6H); $^{13}$C NMR (100.6 MHz, CDCl$_3$) δ 213.6, 143.2, 142.4, 136.3, 129.5, 128.3, 123.1, 51.2, 47.6, 37.5, 30.4, 28.3, 22.6; GC-MS (M)+ calcd for C$_{15}$H$_{19}$BrO 294.0619, found 294.0617.

(E)-1-(6-bromo-3,4-dihydro-1,1,4,4,7-pentamethylnaphthalen-2(1H)-ylidene)-2-tosylhydrazine (25). To a suspension of 24 (3.0664 g, 10.4 mmol) and p-toluenesulfonylhydrazide (2.2158 g, 11.9 mmol) in methanol (61 mL) was added p-toluenesulfonic acid monohydrate (0.4977 g, 2.616 mmol) and the reaction solution was stirred and refluxed under nitrogen for 24 h. The reaction was then cooled to room temperature, and then it was stirred in a salt-water ice-bath at −15° C. for 1 hour, and the resulting precipitate was filtered and rinsed with cold methanol to afford 25 as a white crystalline solid (2.41 g, 50%): $^1$H NMR (400 MHz, CDCl$_3$) δ 8.03 (br s, 1H), 7.84 (d, J=8.0, 2H), 7.34 (s, 1H), 7.28 (d, J=8.4, 2H), 7.12 (s, 1H), 2.41 (s, 2H), 2.38 (s, 3H), 2.33 (s, 3H), 1.37 (s, 6H), 1.08 (s, 6H); $^{13}$C NMR (100.6 MHz, CDCl$_3$) δ 163.2, 144.0, 143.1, 142.7, 136.0, 134.9, 129.3, 128.3, 128.0, 122.7, 42.8, 36.8, 36.2, 29.9, 29.89, 22.5, 21.5; LC-MS (M+H)+ calcd for C$_{22}$H$_{28}$N$_2$O$_2$SBr 463.1055, found 463.1048.

6-Bromo-1,1,4,4,7-pentamethyl-1,4-dihydronaphthalene (26). To a suspension of 25 (1.0127 g, 2.19 mmol) in MTBE (20 mL) was added a methyl lithium LiBr complex solution (1.5 M) in ether (4.40 mL, 6.60 mmol) at room temperature with stirring under nitrogen. The solution turned yellow with the evolution of gas (presumably nitrogen), and a fine off-white precipitate formed. The heterogenous solution was stirred for 1 h, cooled to 0° C., and then quenched with water (25.0 mL). The reaction was extracted with ethyl acetate, and the organic layers were combined, washed with brine, dried over sodium sulfate, filtered and concentrated in vacuo to give a crude off-white solid that was purified by column chromatography (150 mL SiO$_2$, hexanes) to give 26 (0.5463 g, 90%) as a white solid (m.p. 103-105° C.): $^1$H NMR (400 MHz, CDCl$_3$) δ 7.50 (s, 1H), 7.21 (s, 1H), 5.49 (s, 2H), 2.38 (s, 3H), 1.32 (s, 12H); $^{13}$C NMR (100.6 MHz, CDCl$_3$) δ 142.3, 141.8, 135.0, 132.7, 132.6, 129.8, 128.5, 122.4, 35.0, 34.9, 32.5, 32.4, 22.6; GC-MS (M)+ calcd for C$_{15}$H$_{19}$Br 278.0670, found 278.0655.

3,4-Dihydro-1,1,4,4,7-pentamethylnaphthalen-2(1H)-one (23). A modified procedure of Boehm and co-workers was used. (Zhang, L.; Badea, B. A.; Enyeart, D.; Berger, E. M.; Mais, D. E.; Boehm, M. F. "Synthesis of Isotopically Labeled 4-[1-(3,5,5,8,8-Pentamethyl-5,6,7,8-tetrahydro-2-naphthyl)ethenyl]benzoic Acid (LGD1069)" *Journal of Labelled Compounds and Radiopharmaceuticals* 1995, 36, 701-712.) To a 100 mL round bottom flask charged with dihydro-2,2,5,5-tetramethylfuran-3(2H)-one (22) (2.4 g, 17 mmol) and toluene (10.0 mL, 94 mmol) at 0° C. was added aluminum chloride (4.55 g, 34 mmol) in one portion with stirring. The reaction was stirred at 0° C. for 30 min, then (4-Cyanophenyl)-N-methoxy-N-methylformamide (28). The method of Faul et al. was used. To a suspension of N,O-dimethylhydroxyamine hydrochloride (7.07 g, 72.5 mmol) and $K_2CO_3$ (10.0 g, 72.5 mmol) in ACN (100 mL) and water (50 mL) was added 4-cyanobenzoyl chloride (27) (8.00 g, 48.3 mmol), and the reaction was stirred for 2 h at room temperature. The reaction solution was poured into water (50 mL) and extracted with ethyl acetate. The combined organic layers were washed with brine, dried over sodium sulfate, and concentrated in vacuo to give a crude solid that was purified by column chromatography (250 mL $SiO_2$, hexanes:ethyl acetate 45:55 to 1:1) to give 28 (8.12 g, 88%) as a white crystalline solid: $^1$H NMR (400 MHz, $CDCl_3$) δ 7.76 (d, J=8.4, 2H), 7.69 (d, J=8.4, 2H), 3.50 (s, 3H), 3.36(s, 3H); $^{13}$C NMR (100.6 MHz, $CDCl_3$) δ 167.8, 138.2, 131.8, 128.7, 118.1, 114.0, 61.2, 33.0; GC-MS (M)+ calcd for $C_{10}H_{10}N_2O_2$ 190.0742, found 190.0739.

4-[(3,5,5,8,8-Pentamethyl-2-5,8-dihydronaphthyl)carbonyl]benzenecarbonitrile (29). The method of Faul et al. was followed. To a solution of 25 (2.00 g, 7.16 mmol) in THF (25 mL) at −78° C. under nitrogen was added a 1.6 M solution of n-BuLi in hexanes (5.40 mL, 8.60 mmol) over 10 min and the solution was stirred for 20 min at −78° C. This reaction solution was transferred via air-tight syringe to a solution of 28 (1.23 g, 6.47 mmol) in THF (10 mL) at −78° C., and the combined mixture was stirred for 15 min at −78° C. and then warmed to room temperature before 1.0 N HCl (75 mL) was added to quench the reaction. The solution was poured into ethyl acetate, the layers were separated, and the aqueous layer was extracted with ethyl acetate. The combined organic layers were washed with brine, dried over sodium sulfate, and concentrated in vacuo to give a crude product that was purified by column chromatography (150 mL $SiO_2$, hexanes:ethyl acetate 95:5) to give 29 (1.7865 g, 82%) as a white crystalline solid: $^1$H NMR (400 MHz, $CDCl_3$) δ 7.91 (d, J=8.4, 2H), 7.75 (d, J=8.4, 2H), 5.52 (s, 2H), 2.37 (s, 3H), 1.37 (s, 6H), 1.26 (s, 6H); $^{13}$C NMR (100.6 MHz, $CDCl_3$) δ 196.6, 146.2, 141.6, 139.8, 135.0, 134.4, 132.6, 132.6, 129.2, 128.0, 118.0, 115.9, 35.3, 34.8, 32.4, 32.3, 20.0; GC-MS (M)+ calcd for $C_{23}H_{23}NO$ 329.1780, found 329.1788.

4-[(3,5,5,8,8-Pentamethyl-2-5,8-dihydronaphthyl)carbonyl]benzoic Acid (30). The method of Faul et al. was followed. To a heterogeneous solution of 29 (1.62 g, 4.92 mmol) in 2-methoxyethanol (20 mL) was added a solution of KOH (1.64 g, 24.5 mmol) in water (10 mL). The reaction was heated in an oil bath at reflux temperature and stirred under nitrogen for 16 h. The reaction was allowed to cool to room temperature before it was quenched with 1 N HCl (50 mL). The solution was poured into ethyl acetate, the layers were separated, and the aqueous layer was extracted with ethyl acetate. The combined organic layers were washed with brine, dried over sodium sulfate, and concentrated in vacuo with additional toluene to azeotrope off 2-methoxyethanol to give 30 (1.65 g, 96%) as a white powder: $^1$H NMR (400 MHz, $CDCl_3$) δ 13.36 (br s, 1H), 8.08 (d, J=8.4, 2H), 7.80 (d, J=8.4, 2H), 7.42 (s, 1H), 7.34 (s, 1H), 5.54 (s, 2H), 2.25 (s, 3H), 1.33 (s, 6H), 1.22 (s, 6H); $^{13}$C NMR (100.6 MHz, $CDCl_3$) δ 197.0, 166.6, 145.1, 140.7, 139.3, 135.2, 134.5, 133.9, 132.6, 132.5, 129.7, 129.6, 128.8, 127.1, 34.9, 34.5, 32.0, 19.4; LC-MS (M+H)+ calcd for $C_{23}H_{25}O_3$ 349.1804, found 349.1805.

4-[1-(3,5,5,8,8-Pentamethyl-2-5,8-dihydronaphthyl)vinyl]benzoic Acid (2). The procedure of Faul et al. was followed. To a 100 mL round bottom flask charged with a 3.0 M solution of MeMgCl (1.53 mL, 4.60 mmol) was added THF (3 mL), and the solution was cooled to −10° C. in a salt-water ice bath with stirring under nitrogen. To this solution was added a solution of 30 (0.40 g, 1.15 mmol) in THF (4 mL), dropwise, and the reaction was stirred at 0° C. for 4 h. The reaction was quenched with 1.0 N HCl (15 mL), the solution was extracted with ethyl acetate, and the combined organic layers were washed with brine, dried over sodium sulfate, filtered and concentrated in vacuo to give an intermediate alcohol that was used without further purification. The intermediate alcohol was dissolved in toluene (30 mL), and to this solution was added p-toluenesulfonic acid monohydrate (0.02 g, 0.116 mmol), and the solution was refluxed into a Dean-Stark apparatus pre-filled with toluene. After the solution was refluxed for 2 h, it was cooled to room temperature and poured into ethyl acetate and water. The aqueous layer was extracted with ethyl acetate, and the combined organic layers were washed with brine, dried over sodium sulfate, filtered and concentrated in vacuo to give a crude product that was column chromatography (25 mL $SiO_2$, ethyl acetate) to give 2 (0.3628 g, 91%) as a white crystalline solid (m.p. 210-213° C.): $^1$H NMR (400 MHz, $CDCl_3$) δ 11.98 (br s, 1H), 8.05 (d, J=8.8, 2H), 7.40 (d, J=8.4, 2H), 7.20 (s, 1H), 7.15 (s, 1H), 5.86 (d, J=1.2, 1H), 5.54 (s, 2H), 5.38 (d, J=1.2, 1H), 1.99 (s, 3H), 1.37 (s, 6H), 1.34 (s, 6H); $^{13}$C NMR (100.6 MHz, $CDCl_3$) δ 172.0, 149.0, 146.3, 142.0, 140.1, 138.2, 133.1, 133.1, 133.0, 130.3, 128.0, 127.7, 127.7, 126.6, 117.3, 35.0, 34.9, 32.7, 32.6, 20.0; LC-MS (M+H)+ calcd for $C_{24}H_{27}O_2$ 347.2011, found 347.1997. Anal. Calcd for $C_{24}H_{26}O_2$: C, 83.20; H, 7.56. Found: C, 82.73; H, 7.54.

The invention will now be illustrated by the following non-limiting Examples.

EXAMPLES

Example 1

Preparation of 2-(1-(1,2,3,4-tetrahydro-1,1,4,4,6-pentamethylnaphthalen-7-yl)vinyl)pyrimidine-5-carboxylic acid (4) and 2-[1-(3,5,5,8,8-pentamethyl-5,6,7,8-tetrahydronaphthalen-2-yl)cyclopropyl]pyrimidine-2-carboxylic Acid (5)

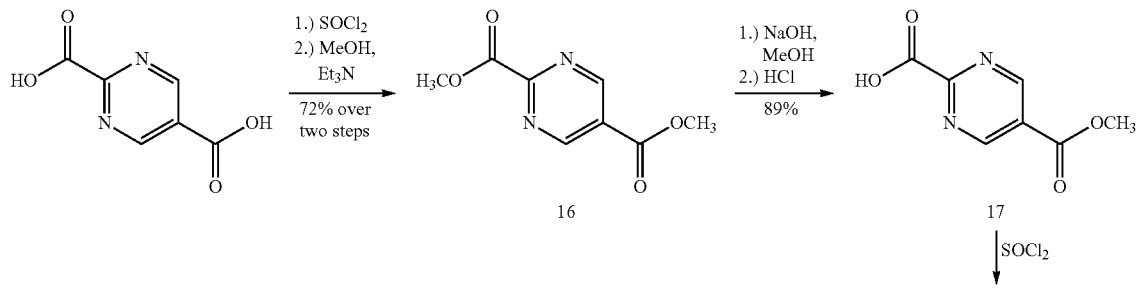

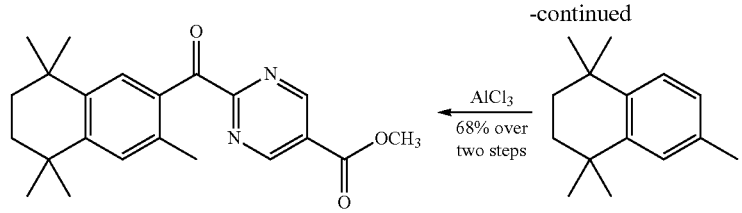

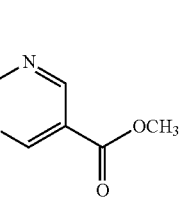

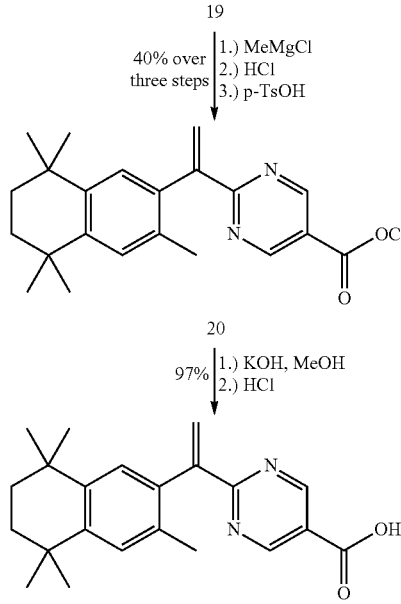

Dimethyl pyrimidine-2,5-dicarboxylate (16). To a 100 mL round bottom flask charged with pyrimidine-2,5-dicarboxylic acid (5.067 g, 30.1 mmol) was slowly added thionyl chloride (21 mL, 290 mmol) and 3 drops of DMF, and the reaction was refluxed in an oil bath at 85° C. for 3 h. Excess thionyl chloride was removed in vacuo, and benzene (20 mL) was added to the crude solid, and the benzene was removed in vacuo to give crude pyrimidine-2,5-dicarboyl dichloride that was used without further purification. To the crude pyrimidine-2,5-dicarboyl dichloride was added toluene (13.6 mL), and this solution was added dropwise to a solution of triethylamine (16.5 mL, 118 mmol) in methanol (86 mL). After stirring for 1 h at room temperature, the reaction was quenched with 1 N HCl (120 mL). The reaction was poured into ethyl acetate (80 mL), the layers were separated, and the aqueous layer was extracted with ethyl acetate. The combined organic layers were washed with saturated $NaHCO_3$ (75 mL) and brine, dried over sodium sulfate, and removed in vacuo to give crude 16. Crude 16 was purified by column chromatography (250 mL $SiO_2$, hexanes:ethyl acetate 2:3) to give 16 (4.26 g, 72%) as a colorless, crystalline solid (m.p. 140-142° C.):$^1$H NMR (400 MHz, $CDCl_3$) δ 9.40 (s, 2H), 4.07 (s, 3H), 3.99 (s, 3H); $^{13}$C NMR (100.6 MHz, $CDCl_3$) δ 163.0, 162.9, 158.8, 158.3, 125.4, 53.8, 53.0; GC-MS (M)+ calcd for $C_8H_8N_2O_4$ 196.0484, found 196.0485.

5-(Methoxycarbonyl)pyrimidine-2-carboxylic acid (17). To a suspension of dimethyl pyrimidine-2,5-dicarboxylate (16) (3.34 g, 17.0 mmol) in methanol (30 mL) was added sodium hydroxide pellets (0.748 g, 18.7 mmol), and the heterogeneous reaction was stirred and refluxed for 4 h. After cooling to 65° C., 2.0 N HCl (14 mL, 28 mmol) was slowly added. The reaction solution was allowed to cool to room temperature, and then it was concentrated in vacuo to give a solid. The solid was filtered with cold water, and the filter-cake was washed with a small amount of cold water to give a white crystalline solid (m.p. 152-154° C.) (2.765 g, 89%):$^1$H NMR (400 MHz, d6-DMSO) δ 13.89 (br s, 1H), 9.39 (s, 2H), 3.97 (s, 3H); $^{13}$C NMR (100.6 MHz, d6-DMSO) δ 164.3, 163.4, 159.6, 158.4, 124.8, 52.9; GC-MS (M)+ calcd for $C_7H_6N_2O_4$ 182.0328, found 182.0335.

Methyl 2-[(3,5,5,8,8-Pentamethyl-5,6,7,8-tetrahydronaphthalen-2-yl)carbonyl]pyrimidine-5-carboxylate (19). Methyl 2-(chlorocarbonyl)-pyrimidine-5-carboxylate (18) was synthesized by refluxing 5-(methoxycarbonyl)pyrimidine-2-carboxylic acid (17) (1.22 g, 6.70 mmol) in thionyl chloride (12.0 mL, 165 mmol) in a 100 mL one-neck round bottom flask fitted with a water-cooled reflux condenser. Excess thionyl chloride was removed in vacuo to give crude 18 as an off-white solid, and this solid was dissolved in dry benzene (ca. 20 mL) and evaporated to dryness to remove residual thionyl chloride. The acid chloride 18 was dried on high vacuum to remove residual benzene. To a 2-neck, 50 mL round bottom flask equipped with a reflux condenser and magnetic stir-bar was added 12 (1.45 g, 7.16 mmol) followed by a solution of crude acid chloride 18 (6.70 mmol) in DCM (15 mL). Aluminum chloride (2.20 g, 16.5 mmol) was added to the reaction solution at room temperature slowly, with stirring, and the reaction solution turned from colorless to red accompanied by the evolution of gas and heat. The reaction was stirred for 5 min then heated to reflux for 15 min. The reaction was judged to be complete by TLC, and the solution was poured into an ice solution (25 mL) acidified with a 20% HCl solution (8 mL) and ethyl acetate was added (13 mL). The aqueous and organic layers were separated, and the aqueous layer was extracted with ethyl acetate (15 mL, twice). The combined organics were washed with water and brine, dried over sodium sulfate, filtered and concentrated to give crude 19. Crude 19 was purified by column chromatography (250 mL $SiO_2$, hexanes:ethyl acetate 95:5 to 85:15) to give 19 (1.677 g, 68%) as an off-white, crystalline solid: $^1$H NMR (400 MHz, $CDCl_3$) δ 9.42 (s, 2H), 7.40 (s, 1H), 7.21 (s, 1H), 4.03 (s, 3H), 2.43 (s, 3H), 1.66 (s, 4H), 1.28 (s, 6H), 1.17 (s, 6H); $^{13}$C NMR (100.6 MHz, $CDCl_3$) δ 192.8, 165.9, 163.5, 158.4, 150.3, 142.0, 136.7, 131.9, 130.8, 130.0, 124.0, 52.9, 34.7, 34.6, 34.4, 33.8, 31.6, 31.4, 20.9; LC-MS (M+H)+ calcd for $C_{22}H_{27}N_2O_3$ 367.2022, found 367.2017.

Methyl 2-[(3,5,5,8,8-Pentamethyl-5,6,7,8-tetrahydronaphthalen-2-yl)ethenyl]pyrimidine-5-carboxylate (20). To a 100 mL round bottom flask charged with 19 (1.0373 g, 2.83 mmol) was added toluene (10 mL) and the solution was cooled in a salt-water ice bath to −15° C. with stirring, under nitrogen. To this solution was added a 22 wt % solution of MeMgCl in THF (1.20 mL, 3.60 mmol), and the reaction was stirred for 15 min at −15° C. and then warmed to room temperature and stirred for 35 min before quenching with 1N HCl (7 mL, 7 mmol). The reaction mixture was then separated and the aqueous layer was extracted with ethyl acetate. The combined organic layers filtered, and a small yellow filter-cake was dissolved in chloroform and added to the organic filtrate, and combined organic filtrate was concentrated in vacuo to give a crude alcohol intermediate that was used without further purification. To this crude intermediate in a 100 mL round bottom flask was added p-toluenesulfonic acid monohydrate (0.5247 g, 2.76 mmol) and toluene (40 mL), and the reaction was refluxed for 3 h into a Dean-Stark apparatus half-filled with toluene (6 mL). After the reaction had cooled to room temperature, it was added to a solution of sodium carbonate (0.78 g) in water (15 mL), shaken vigorously, and the layers were separated. The aqueous layer was extracted with ethyl acetate, and the combined organic layers were washed with brine, dried over sodium sulfate, filtered and concentrated in vacuo, to give a crude brown product that was purified by column chromatography (150 mL $SiO_2$, hexanes:ethyl acetate 97.5:2.5 to 95:5) to give 20 (0.4127 g, 40%) as a white, fiber-like solid: $^1$H NMR (400 MHz, $CDCl_3$) δ 9.25 (s, 2H), 7.17 (s, 1H), 7.11 (s, 1H), 6.83 (d, J=2.0, 1H), 5.80 (d, J=2.0, 1H), 3.97 (s, 3H), 1.98 (s, 3H), 1.69 (s, 4H), 1.31 (s, 6H), 1.28 (s, 6H); $^{13}$C NMR (100.6 MHz, $CDCl_3$) δ 168.6, 164.4, 158.2, 148.3, 144.4, 142.1, 136.3, 132.7, 128.0, 127.9, 126.7, 121.1, 52.5, 35.1, 34.0, 33.8, 31.9, 31.8, 20.0; LC-MS (M+H)+ calcd for $C_{23}H_{29}N_2O_2$ 365.2229, found 365.2232.

Methyl 2-[(3,5,8,8-Pentamethyl-5.6,7,8-tetrahydronaphthalen-2-yl)cyclopropyl]pyrimidine-5-carboxylate (21). To a suspension of trimethylsulfoxonium iodide (0.365 g, 1.66 mmol) in DMSO (1.2 mL) was added a 20 wt % solution of potassium tert-butoxide in THF (0.94 mL, 1.67 mmol). A solution of 20 (0.4062 g, 1.11 mmol) in THF (4.8 mL) was added dropwise over 20 min at 30-34° C. with stirring. The reaction was stirred for 60 min at 35° C., then cooled to room temperature and quenched with 1N HCl (5 mL). The layers were separated and the aqueous layer was extracted with ethyl acetate. The combined organic layers were washed with brine, dried over sodium sulfate, and concentrated to give an off-white crude solid that was purified by column chromatography (150 mL $SiO_2$, hexanes:ethyl acetate 97.5:2.5 to 90:10) to give 21 (0.2884 g, 68%) as a white crystalline solid: $^1$H NMR (400 MHz, $CDCl_3$) δ 9.07 (s, 2H), 7.23 (s, 1H), 7.09 (s, 1H), 3.92 (s, 3H), 2.12 (s, 3H), 1.87-1.88 (m, 2H), 1.67 (s, 4H), 1.46-1.47 (m, 2H), 1.29 (s, 6H), 1.27 (s, 6H); $^{13}$C NMR (100.6 MHz, $CDCl_3$) δ 176.8, 164.7, 157.7, 143.2, 141.8, 136.9, 135.9, 128.6, 127.8, 119.9, 52.3, 35.2, 34.0, 33.9, 31.9, 31.8, 31.7, 21.6, 19.4; LC-MS (M+H)+ calcd for $C_{24}H_{31}N_2O_2$ 379.2386, found 379.2385.

2-(1-(1,2,3,4-Tetrahydro-1,1,4,4,6-pentamethylnaphthalen-7-yl)vinyl)pyrimidine-5-carboxylic acid (4). To a suspension of 20 (0.828 g, 2.27 mmol) in methanol (15.0 mL) was added a solution of KOH (0.3627 g) in water (0.54 mL), and the reaction was refluxed at 85° C. for 1 h. The reaction solution was cooled to room temperature and quenched with 20% HCl (60 mL). The crude precipitate was filtered and dried to give a crude white product (0.7741 g, 97%) that was recrystallized from hexanes:ethyl acetate 4:1 to give the pure 4 as a white crystalline solid (0.3869 g, 48%): $^1$H NMR (400 MHz, $CDCl_3$) δ 10.11 (br s, 1H), 9.31 (s, 2H), 7.17 (s, 1H), 7.12 (s, 1H), 6.86 (d, J=1.6, 1H), 5.86 (d, J=1.6, 1H), 1.99 (s, 3H), 1.68 (s, 4H), 1.28 (s, 6H), 1.27 (s, 6H); $^{13}$C NMR (100.6 MHz, $CDCl_3$) δ 169.0, 168.2, 158.8, 148.0, 144.5, 142.2, 136.0, 132.7, 128.0, 127.9, 127.3, 120.7, 35.1, 34.0, 33.8, 31.9, 31.8, 20.0; LC-MS (M+H)+ calcd for $C_{22}H_{27}N_2O_2$ 351.2073, found 351.2082. Anal. Calcd for $C_{22}H_{26}N_2O_2$: C, 75.40; H, 7.48; N, 7.99. Found: C, 75.35; H, 7.54; N, 7.91.

2-[1-(3,5,5,8,8-Pentamethyl-5,6,7,8-tetrahydronaphthalen-2-yl)cyclopropyl]pyrimidine-2-carboxylic Acid (5). To a suspension of 21 (0.287 g, 0.758 mmol) in methanol (5.0 mL) was added a solution of KOH (0.126 g) in water (0.18 mL), and the reaction was refluxed at 85° C. for 1 h. The reaction solution was cooled to room temperature and quenched with 20% HCl (32 mL). The crude precipitate was filtered and dried to give a crude white product (0.2568 g, 92%) that was recrystallized from hexanes:ethyl acetate 4:1 to give the pure 5 as a white crystalline solid (0.2433 g, 88%): $^1$H NMR (400 MHz, $CDCl_3$) δ 9.18 (s, 2H), 7.23 (s, 1H), 7.09 (s, 1H), 2.13 (s, 3H), 1.90-1.91 (m, 2H), 1.66 (s, 4H), 1.50-1.51 (m, 2H), 1.27 (s, 6H), 1.26 (s, 6H); $^{13}$C NMR (100.6 MHz, $CDCl_3$) δ 177.6, 168.6, 158.3, 143.3, 141.9, 136.6, 135.9, 128.6, 127.9, 119.2, 35.2, 34.0, 33.9, 32.0, 31.9, 31.8, 22.1, 19.4; LC-MS (M+H)+ calcd for $C_{23}H_{29}N_2O_2$ 365.2229, found 365.2225. Anal. Calcd for $C_{23}H_{28}N_2O_2$: C, 75.79; H, 7.74; N, 7.69. Found: C, 75.67; H, 7.95; N, 7.32.

Example 2

Preparation of (E)-3-(3-(1,2,3,4-tetrahydro-1,1,4,4, 6-pentamethylnaphthalen-7-yl)-4-methylphenyl) acrylic acid (6)

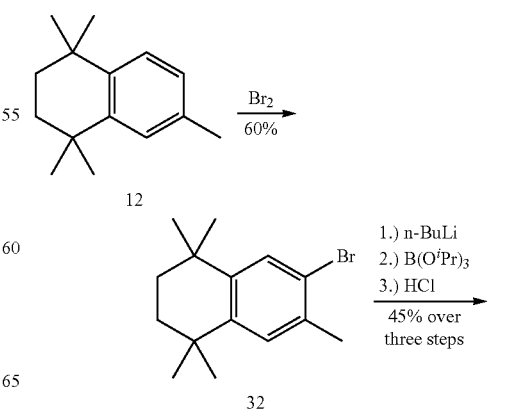

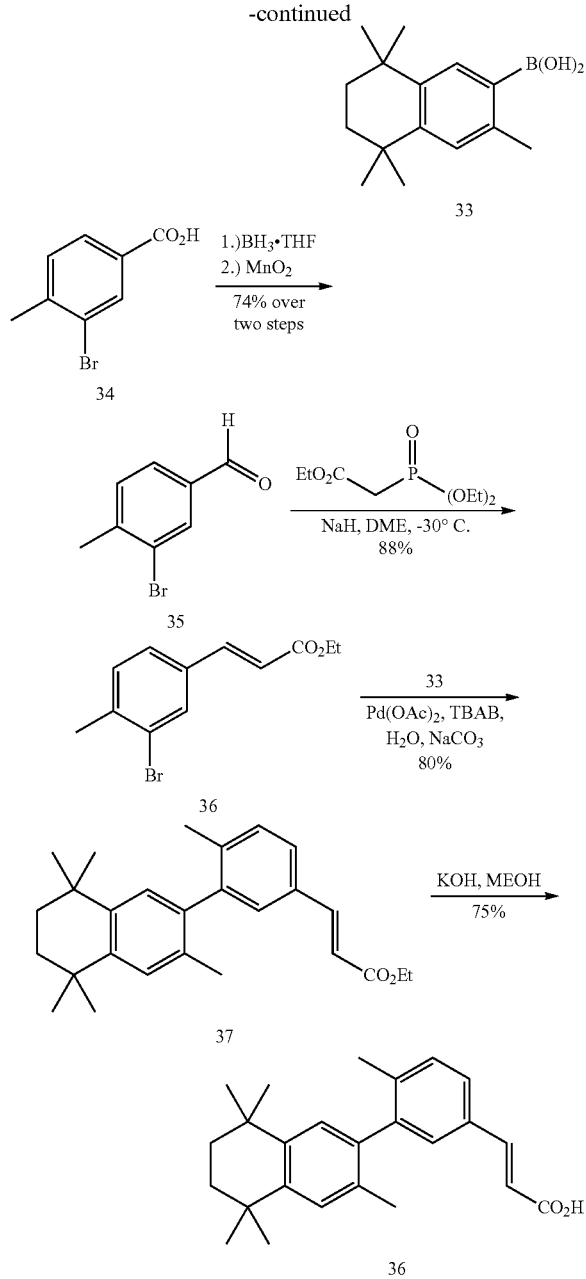

6-Bromo-1,2,3,4-tetrahydro-1,1,4,4,7-pentamethylnaphthalene (32). The method of Dawson et al. was used to synthesize 32 (Dawson, M. I., et al, "Conformational Effects on Retinoid Receptor Selectivity. 2. Effects of Retinoid Bridging Group on Retinoid X Receptor Activity and Selectivity" *J. Med. Chem.* 1995, 38, 3368-3383). To a solution of 12 (1.32 g, 6.52 mmol) in chloroform (6.0 mL) was added bromine (0.5 mL, 9.71 mmol) at room temperature, and the reaction was stirred for 30 min and then diluted with ethyl acetate. The solution was poured into an aqueous saturated solution of $Na_2SO_3$ and the biphasic mixture was shaken, the layers were separated and the aqueous layer was extracted with ethyl acetate. The combined organic layers were washed with brine, dried over sodium sulfate and concentrated in vacuo to give an oil that was purified by column chromatography (150 mL $SiO_2$, ethyl acetate) to give an inseparable 2:1 mixture of 32:12 (1.679 g, 60% yield for 32) as a white crystalline solid: $^1$H NMR (400 MHz, $CDCl_3$) δ 7.42 (s, 1H), 7.14 (s, 1H), 2.34 (s, 3H), 1.66 (s, 4H), 1.27 (s, 12H); GC-MS (M)+ calcd for $C_{15}H_{21}Br$ 280.0827, found 280.0812.

5,6,7,8-Tetrahydro-3,5,5,8,8-pentamethylnaphthalen-2-yl-2-boronic acid (33). The method of Faul et al. was used. To a 100 mL round bottom flask containing THF (30 mL) was added a 1.6 M solution of n-BuLi in hexanes (8.0 mL, 12.8 mmol), and the resulting solution was cooled in a dry-ice acetone bath to −78° C. with stirring, under nitrogen. To this solution was added a solution of the 2:1 mixture of 32:12 (3.3587 g, 7.88 mmol) in THF (8 mL) over 20 min and the reaction was stirred at −78° C. for 10 min, and a mixture of triisopropylborate (4.9 mL, 21.3 mmol) in THF (10 mL) was added dropwise over 20 min. The reaction was stirred at −78° C. for 1 h and then warmed to room temperature and stirred for 2 h. The reaction was then quenched with 3 N HCl (35 mL), and after stirring for 2 h, it was poured into ethyl acetate, the layers were separated, and the aqueous layer was extracted with ethyl acetate. The combined organic layers were washed with brine, dried over sodium sulfate, and concentrated in vacuo to give a crude product that was purified by column chromatography (150 mL $SiO_2$, ethyl acetate:hexanes 1:3) to give 33 (0.8838 g, 45%) as a white crystalline solid: $^1$H NMR (400 MHz, $CDCl_3$) δ 8.29 (s, 1H), 7.21 (s, 1H), 2.82 (s, 3H), 1.72 (s, 4H), 1.34 (s, 6H), 1.33 (s, 6H); $^{13}$C NMR (100.6 MHz, $CDCl_3$) δ 149.4, 142.8, 141.4, 136.3, 128.5, 35.1, 35.0, 34.3, 33.8, 31.8, 31.5, 22.6.

3-Bromo-4-methylbenzaldehyde (35). The method of Adams and co-workers was followed (Adams, N. D., et al., "Discovery of GSK1070916, a Potent and Selective Inhibitor of Aurora B/C Kinase" *J. Med. Chem.* 2010, 53, 3973-4001). To a solution of 3-bromo-4-methylbenzoic acid (34) (5.08 g, 23 mmol) in THF (50 mL) stirring under nitrogen at 0° C. was added a 1 M borane·THF solution (34.6 mL, 34.6 mmol) dropwise. The reaction was warmed to room temperature, stirred for 18 h, then cooled to 0° C. and quenched by the slow addition of water (10 mL). The reaction was warmed to room temperature, and the solvents were removed in vacuo. The crude product was dissolved in ethyl acetate, washed with a 1 M aqueous sodium carbonate solution, then brine, and the organic layer was dried over sodium sulfate, and concentrated in vacuo to give a benzyl alcohol product (4.75 g, 100%) that was used without further purification: $^1$H NMR (400 MHz, $CDCl_3$) δ 7.52 (d, J=0.8, 1H), 7.20 (d, J=8.0, 1H), 7.17 (dd, J=7.6, 1.6, 1H), 4.61 (s, 2H), 2.38 (s, 3H), 2.05 (br s, 1H);$^{13}$C NMR (100.6 MHz, $CDCl_3$) δ 140.1, 137.0, 130.8, 130.7, 125.8, 124.9, 64.2, 22.5. To a solution of the benzyl alcohol intermediate (4.5 g, 22.4 mmol) in chloroform (100 mL) was added manganese dioxide (15 g, 172 mmol). The reaction was refluxed with stirring in an oil bath at 70° C. for 18 h. Then it was filtered through celite and solvents were removed in vacuo to give a crude product that was purified by column chromatography (150 mL $SiO_2$, ethyl acetate:hexanes 1:9) to give 35 (3.2974 g, 74%) as a white crystalline solid: $^1$H NMR (400 MHz, $CDCl_3$) δ 9.91 (s, 1H), 8.02 (d, J=1.6, 1H), 7.70 (dd, J=7.6, 1.6, 1H), 7.39 (d, J=8.0, 1H), 2.47 (s, 3H); $^{13}$C NMR (100.6 MHz, $CDCl_3$) δ 190.4, 145.1, 135.8, 133.4, 131.3, 128.3, 125.6, 23.4; GC-MS (M)+ calcd for $C_8H_7OBr$ 197.9680, found 197.9665.

(E)-ethyl 3-(3-bromo-4-methylphenyl)acrylate (36). To a solution of a 60% dispersion of NaH in mineral oil (0.29 g, 7.25 mmol) in DME (2 mL) at −30° C. was added a solution of ethyl 2-phosphonoacetate (1.46 mL, 7.29 mmol) in DME (13 mL), and the mixture was stirred at this temperature for 30 min. To this solution was added a solution of 35 (1.32 g, 6.63 mmol) in DME (3 mL), and the reaction was stirred at −30° C. for 1.5 h and then poured into water (50 mL) and extracted with ethyl acetate. The combined organic layers were washed with an aqueous saturated NH$_4$Cl solution and then brine, dried over sodium sulfate, filtered and concentrated in vacuo to give a crude product that was purified by column chromatography (150 mL SiO$_2$, ethyl acetate: hexanes 1:9) to give 36 (1.576 g, 88%) as a colorless crystalline solid: $^1$H NMR (400 MHz, CDCl$_3$) δ 7.69 (d, J=1.6, 1H), 7.57 (d, J=16.0, 1H), 7.35 (dd, J=8.0, 1.6, 1H), 7.23 (d, J=7.6, 1H), 6.38, (d, J=16.0, 1H), 4.25 (q, J=7.2, 2H), 2.41 (s, 3H), 1.33 (t, J=7.2, 3H); $^{13}$C NMR (100.6 MHz, CDCl$_3$) δ 166.7, 142.8, 140.1, 133.9, 131.6, 131.1, 126.8, 125.3, 118.6, 60.5, 22.9, 14.2; LC-MS (M+H)+ calcd for C$_{12}$H$_{14}$O$_2$Br 269.0177, found 269.0171.

(E)-ethyl 3-(3-(1,2,3,4-tetrahydro-1,1,4,4,6-pentamethyl-naphthalen-7-yl)-4-methylphenyl)acrylate (37). To a 50 mL Schlenk flask charged with bromide 36 (0.4317 g, 1.60 mmol), boronic acid 33 (0.4010 g, 1.63 mmol), TBAB (0.52 g), Na$_2$CO$_3$ (0.51 g, 4.81 mmol), and water (3.7 mL), was added Pd(OAc)$_2$ (0.0203 g, 0.09 mmol), and the flask was evacuated and back-filled with nitrogen three times. The reaction was stirred at room temperature for 15 min and then placed in an oil bath pre-heated to 150° C. and stirred for 5 min. The reaction was allowed to cool to room temperature, and the black residue was taken up in ethyl acetate and water. The layers were separated, and the aqueous layer was extracted with ethyl acetate. The combined organic layers were washed with brine, dried over sodium sulfate, filtered, and concentrated in vacuo to give a crude product that was purified by column chromatography (150 mL SiO$_2$, ethyl acetate:hexanes 1:9) to give 37 (0.5032 g, 80%) as a colorless oil: $^1$H NMR (400 MHz, CDCl$_3$) δ 7.68 (d, J=16.0, 1H), 7.41 (dd, J=8.0, 2.0, 1H), 7.33 (d, J=1.6, 1H), 7.27 (d, J=8.0, 1H), 7.16 (s, 1H), 7.00 (s, 1H), 6.39, (d, J=16.0, 1H), 4.25 (q, J=7.2, 2H), 2.09 (s, 3H), 2.01 (s, 3H), 1.70 (s, 4H), 1.33 (t, J=7.2, 3H), 1.32 (s, 6H), 1.26 (s, 3H), 1.24 (s, 3H); $^{13}$C NMR (100.6 MHz, CDCl$_3$) δ 171.1, 167.2, 144.6, 143.8, 143.1, 142.5, 142.1, 141.6, 139.0, 138.8, 137.7, 132.8, 132.3, 131.7, 130.3, 129.3, 127.9, 127.6, 127.4, 127.2, 126.6, 117.2, 60.4, 60.3, 35.2, 35.1, 34.0, 33.9, 32.0, 31.9, 31.8, 31.8, 21.0, 20.0, 19.8, 19.5, 14.3, 14.1; LC-MS (M+H)+ calcd for C$_{27}$H$_{35}$O$_2$ 391.2637, found 391.2655.

(E)-3-(1,2,3,4-tetrahydro-1,1,4,4,6-pentamethylnaphthalen-7-yl)-4-methylphenyl)acrylic acid (6). To a 100 mL round bottom flask containing 37 (0.3288 g, 0.84 mmol) suspended in methanol (5.0 mL) was added a solution of KOH (0.1412 g, 2.5 mmol) in water (0.18 mL), and the solution was refluxed in an oil-bath pre-heated to 85° C. for 1 h. The reaction was allowed to cool to room temperature, and acidified with an aqueous 20% HCl solution (28 mL). The resulting precipitate was filtered and washed with copious amounts of water, and the crude white powder was purified by column chromatography (25 mL SiO$_2$, ethyl acetate:hexanes 15:85) to give 6 (0.2295 g, 75%) as a white crystalline solid: $^1$H NMR (400 MHz, CDCl$_3$) δ 7.79 (d, J=16.0, 1H), 7.44 (dd, J=8.0, 1.6, 1H), 7.37 (d, J=1.6, 1H), 7.29 (d, J=7.6, 1H), 7.17 (s, 1H), 7.01 (s, 1H), 6.42, (d, J=16.0, 1H), 2.11 (s, 3H), 2.02 (s, 3H), 1.71 (s, 4H), 1.33 (s, 3H), 1.32 (s, 3H), 1.27 (s, 3H), 1.24 (s, 3H); $^{13}$C NMR (100.6 MHz, CDCl$_3$) δ 172.6, 147.1, 143.8, 142.7, 142.1, 139.7, 137.5, 132.3, 131.4, 130.4, 129.6, 127.7, 126.9, 116.3, 35.2, 35.1, 34.0, 33.9, 32.0, 31.9, 31.8, 20.1, 19.5; LC-MS (M+H)+ calcd for C$_{25}$H$_{31}$O$_2$ 363.2324, found 363.2311. Anal. Calcd for C$_{25}$H$_{30}$O2: C, 82.83; H, 8.34. Found: C, 81.84; H, 8.28.

Example 3

Preparation of (2E)-3-(3-(1,4-dihydro-1,1,4,4,6-pentamethylnaphthalen-7-yl)-4-methylphenyl)acrylic acid (7)

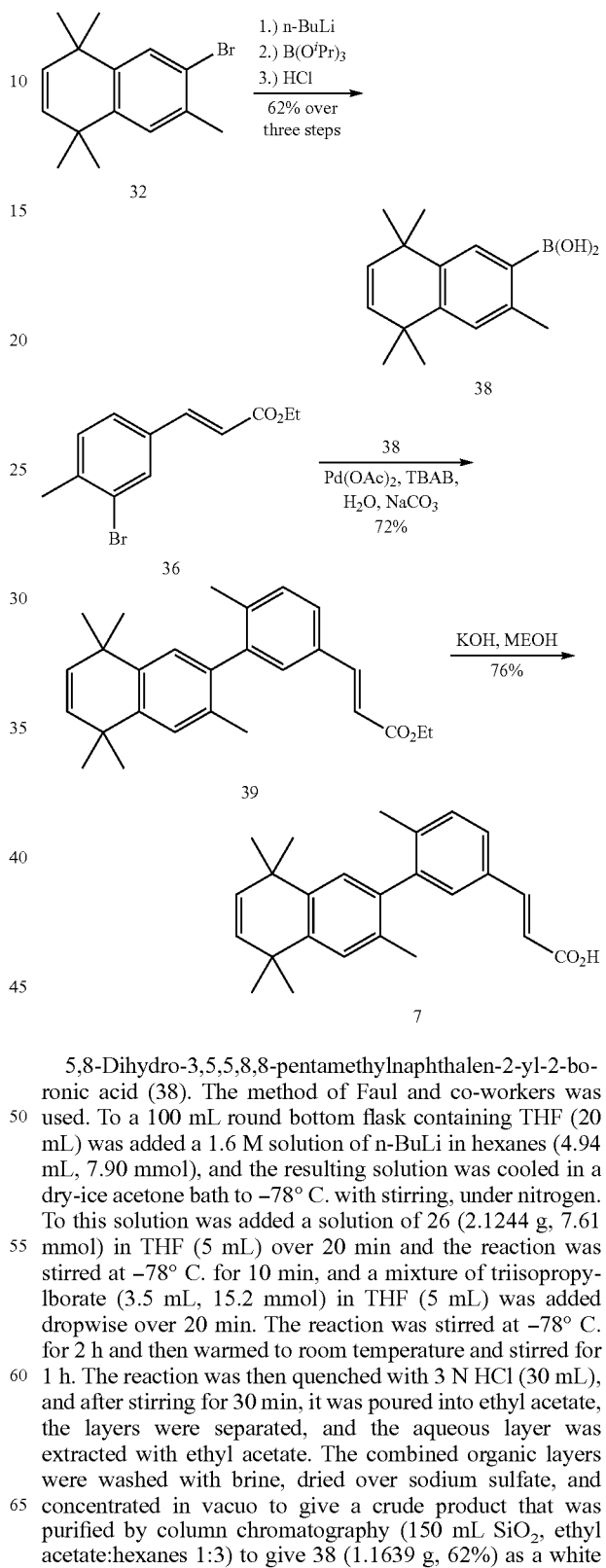

5,8-Dihydro-3,5,5,8,8-pentamethylnaphthalen-2-yl-2-boronic acid (38). The method of Faul and co-workers was used. To a 100 mL round bottom flask containing THF (20 mL) was added a 1.6 M solution of n-BuLi in hexanes (4.94 mL, 7.90 mmol), and the resulting solution was cooled in a dry-ice acetone bath to −78° C. with stirring, under nitrogen. To this solution was added a solution of 26 (2.1244 g, 7.61 mmol) in THF (5 mL) over 20 min and the reaction was stirred at −78° C. for 10 min, and a mixture of triisopropylborate (3.5 mL, 15.2 mmol) in THF (5 mL) was added dropwise over 20 min. The reaction was stirred at −78° C. for 2 h and then warmed to room temperature and stirred for 1 h. The reaction was then quenched with 3 N HCl (30 mL), and after stirring for 30 min, it was poured into ethyl acetate, the layers were separated, and the aqueous layer was extracted with ethyl acetate. The combined organic layers were washed with brine, dried over sodium sulfate, and concentrated in vacuo to give a crude product that was purified by column chromatography (150 mL SiO$_2$, ethyl acetate:hexanes 1:3) to give 38 (1.1639 g, 62%) as a white crystalline solid: $^1$H NMR (400 MHz, CDCl$_3$) δ 8.36 (s, 1H), 7.28 (s, 1H), 5.56 (s, 2H), 2.87 (s, 3H), 1.41 (s, 6H), 1.39 (s, 6H).

(2E)-ethyl 3-(3-(1,4-dihydro-1,1,4,4,6-pentamethylnaphthalen-7-yl)-4-methylphenyl)acrylate (39). To a 50 mL Schlenk flask charged with bromide 36 (0.6506 g, 2.41 mmol), boronic acid 38 (0.2032 g, 0.83 mmol), TBAB (0.26 g), Na$_2$CO$_3$ (0.256 g, 2.42 mmol), and water (1.85 mL), was added Pd(OAc)$_2$ (0.0136 g, 0.061 mmol), and the flask was evacuated and back-filled with nitrogen three times. The reaction was stirred at room temperature for 15 min and then placed in an oil bath pre-heated to 150° C. and stirred for 5 min. The reaction was allowed to cool to room temperature, and the black residue was taken up in ethyl acetate and water. The layers were separated, and the aqueous layer was extracted with ethyl acetate. The combined organic layers were washed with brine, dried over sodium sulfate, filtered, and concentrated in vacuo to give a crude product that was purified by column chromatography (150 mL SiO$_2$, ethyl acetate:hexanes 2.5:97.5) to give 39 (0.2256 g, 72%) as a colorless oil: $^1$H NMR (400 MHz, CDCl$_3$) δ 7.69 (d, J=16.0, 1H), 7.42 (dd, J=8.0, 2.0, 1H), 7.36 (d, J=2.0, 1H), 7.29 (d, J=8.0, 1H), 7.22 (s, 1H), 7.06 (s, 1H), 6.41, (d, J=16.0, 1H), 5.53 (s, 2H), 4.25 (q, J=7.2, 2H), 2.10 (s, 3H), 2.04 (s, 3H), 1.38 (s, 6H), 1.33 (t, J=7.2, 3H), 1.32 (s, 3H), 1.30 (s, 3H); $^{13}$C NMR (100.6 MHz, CDCl$_3$) δ 167.8, 144.5, 142.4, 141.5, 139.8, 139.0, 138.1, 133.1, 133.0, 132.7, 131.8, 130.4, 129.3, 127.3, 126.8, 126.6, 117.3, 60.3, 35.0, 34.9, 32.7, 32.6, 32.6, 20.0, 19.6, 14.3, 14.1; GC-MS (M)+ calcd for C$_{27}$H$_{32}$O$_2$ 388.2402, found 388.2414.

(2E)-3-(3-(1,4-dihydro-1,1,4,4,6-pentamethylnaphthalen-7-yl)-4-methylphenyl)acrylic acid (7). To a 100 mL round bottom flask containing 39 (0.5555 g, 1.43 mmol) suspended in methanol (5.0 mL) was added a solution of KOH (0.2454 g, 4.37 mmol) in water (0.30 mL), and the solution was refluxed in an oil-bath pre-heated to 85° C. for 1 h. The reaction was allowed to cool to room temperature, and acidified with an aqueous 20% HCl solution (50 mL). The resulting precipitate was filtered and washed with copious amounts of water, and the crude white powder was purified by column chromatography (25 mL SiO$_2$, ethyl acetate: hexanes 15:85 to 2:3) to give 7 (0.3917 g, 76%) as a white crystalline solid: $^1$H NMR (400 MHz, CDCl$_3$) δ 7.80 (d, J=15.6, 1H), 7.46 (dd, J=8.0, 2.0, 1H), 7.39 (d, J=1.6, 1H), 7.31 (d, J=8.0, 1H), 7.24 (s, 1H), 7.07 (s, 1H), 6.43, (d, J=16.0, 1H), 5.54 (s, 2H), 2.12 (s, 3H), 2.05 (s, 3H), 1.39 (s, 6H), 1.33 (s, 3H), 1.31 (s, 3H); $^{13}$C NMR (100.6 MHz, CDCl$_3$) δ 172.6, 147.8, 142.5, 141.6, 139.9, 137.9, 133.1, 133.0, 132.7, 131.4, 130.5, 129.6, 127.4, 127.0, 126.8, 116.3, 35.0, 34.9, 32.7, 32.6, 32.6, 20.1, 19.6; GC-MS (M)+ calcd for C$_{25}$H$_{28}$O$_2$ 360.2089, found 360.2089. Anal. Calcd for C$_{25}$H$_{27}$O$_2$: C, 83.29; H, 7.83. Found: C, 82.75; H, 7.83.

Example 4

Preparation of (2E)-3-(3-(1,4-dihydro-1,1,4,4,6-pentamethylnaphthalen-7-yl)-4-hydroxyphenyl) acrylic acid (8)

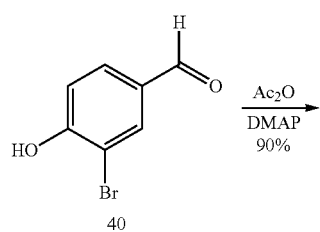

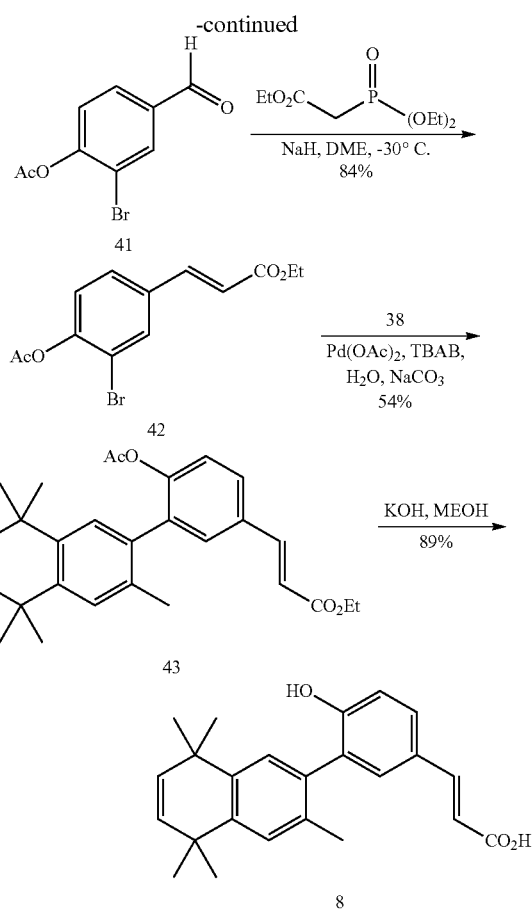

2-Bromo-4-formylphenyl acetate (41). To a 100 mL round bottom flask charged with 3-bromo-4-hydroxybenzaldehyde (2.018 g, 10.0 mmol) was added DMAP (0.066 g, 0.54 mmol) and acetic anhydride (11.0 mL, 116 mmol), a reflux condenser was appended, the apparatus was evacuated and back-filled with nitrogen, and the solution was heated to 135° C. in a pre-heated oil-bath for 8 min. The reaction was cooled to room temperature and then poured into water and extracted with ethyl acetate. The combined organic layers were washed with brine, dried over sodium sulfate, filtered and concentrated in vacuo to give a crude product that was purified by column chromatography (150 mL SiO$_2$, ethyl acetate:hexanes 1:9) to give 41 (2.44 g, 90%) as a white crystalline solid: $^1$H NMR (400 MHz, CDCl$_3$) δ 9.94 (s, 1H), 8.13 (d, J=2.0, 1H), 7.85 (dd, J=8.4, 2.0, 1H), 7.31 (d, J=8.4, 1H), 2.38 (s, 3H); $^{13}$C NMR (100.6 MHz, CDCl$_3$) δ 189.5, 167.8, 152.8, 135.2, 134.5, 129.8, 124.5, 117.4, 20.7; GC-MS (M)+ calcd for C$_9$H$_7$O$_3$Br 241.9579, found 241.9574.

(E)-ethyl 3-(4-acetoxy-3-bromophenyl)acrylate (42). The method of Gronemeyer and co-workers was followed. (Santin, E. P.; Germain, P.; Quillard, F.; Khanwalkar, H.; Rodriguez-Barrios, F.; Gronemeyer, H.; de Lera, A. R.; Bourguet, W. "Modulating Retinoid X Receptor with a Series of (E)-3-[4-Hydroxy-3-(3-alkoxy-5,5,8,8-tetramethyl-5,6,7,8-tetrahydronaphthalen-2-yl)phenyl]acrylic Acids and Their 4-Alkoxy Isomers" *J. Med. Chem.* 2009, 52, 3150-3158.) To a solution of a 60% dispersion of NaH in mineral oil (0.31 g, 7.75 mmol) in DME (2 mL) at −30° C. was added a solution of ethyl 2-phosphonoacetate (1.46 mL, 7.29 mmol) in DME (13 mL), and the mixture was stirred at this temperature for 30 min. To this solution was added a solution of 41 (1.61 g, 6.62 mmol) in DME (3 mL), and the reaction was stirred at −30° C. for 1.5 h and then poured into water (50 mL) and extracted with ethyl acetate. The combined organic layers were washed with an aqueous saturated NH₄Cl solution and then brine, dried over sodium sulfate, filtered and concentrated in vacuo to give a crude product that was purified by column chromatography (150 mL SiO₂, ethyl acetate:hexanes 1:9) to give 42 (1.7598 g, 84%) as a colorless crystalline solid: ¹H NMR (400 MHz, CDCl₃) δ 7.76 (d, J=2.0, 1H), 7.58 (d, J=16.0, 1H), 7.46 (dd, J =8.0, 2.0, 1H), 7.14 (d, J =8.4, 1H), 6.38, (d, J =16.0, 1H), 4.25 (q, J =7.2, 2H), 2.36 (s, 3H), 1.33 (t, J=7.2, 3H); ¹³C NMR (100.6 MHz, CDCl₃) δ 168.2, 166.4, 149.3, 141.9, 133.9, 132.5, 127.9, 124.0, 119.8, 116.8, 60.6, 20.7, 14.2; GC-MS (M)+ calcd for C₁₃H₁₃O₂Br 311.9997, found 311.9988.

(2E)-ethyl 3-(4-acetoxy-3-(1,4-dihydro-1,1,4,4,6-pentamethylnaphthalen-7-yl)phenyl)acrylate (43). To a 50 mL Schlenk flask charged with bromide 42 (0.5038 g, 1.60 mmol), boronic acid 38 (0.4040 g, 1.65 mmol), TBAB (0.52 g), Na₂CO₃ (0.51 g, 4.81 mmol), and water (3.70 mL), was added Pd(OAc)₂ (0.0277 g, 0.123 mmol), and the flask was evacuated and back-filled with nitrogen three times. The reaction was stirred at room temperature for 15 min and then placed in an oil bath pre-heated to 150° C. and stirred for 5 min. The reaction was allowed to cool to room temperature, and the black residue was taken up in ethyl acetate and water. The layers were separated, and the aqueous layer was extracted with ethyl acetate. The combined organic layers were washed with brine, dried over sodium sulfate, filtered, and concentrated in vacuo to give a crude product that was purified by column chromatography (150 mL SiO₂, ethyl acetate:hexanes 5:95 to 3:7) to give 43 (0.3673 g, 54%) as a colorless oil: ¹H NMR (400 MHz, CDCl₃) δ 7.69 (d, J=16.0, 1H), 7.54 (dd, J=8.0, 2.0, 1H), 7.50 (d, J=2.0, 1H), 7.23 (s, 1H), 7.17 (d, J=8.4, 1H), 7.10 (s, 1H), 6.41, (d, J=16.0, 1H), 5.52 (s, 2H), 4.25 (q, J=7.2, 2H), 2.13 (s, 3H), 1.91 (s, 3H), 1.36 (s, 6H), 1.33 (t, J=7.2, 3H), 1.30 (s, 6H); ¹³C NMR (100.6 MHz, CDCl₃) δ 169.1, 166.8, 149.9, 143.5, 142.1, 139.6, 135.6, 133.5, 133.3, 133.0, 132.9, 132.2, 131.0, 127.8, 127.6, 127.5, 123.1, 118.5, 60.5, 35.0, 34.9, 32.6, 20.4, 19.6, 14.2; LC-MS (M+H)+ calcd for C₂₈H₃₃O₄ 433.2379, found 433.2371.

(2E)-3-(3-(1,4-dihydro-1,1,4,4,6-pentamethylnaphthalen-7-yl)-4-hydroxyphenyl)acrylic acid (8). To a 100 mL round bottom flask containing 43 (0.3622 g, 0.87 mmol) suspended in methanol (5.0 mL) was added a solution of KOH (0.3326 g, 5.93 mmol) in water (0.48 mL), and the solution was refluxed in an oil-bath pre-heated to 85° C. for 1 h. The reaction was allowed to cool to room temperature, and acidified with an aqueous 20% HCl solution (50 mL). The resulting precipitate was filtered and washed with copious amounts of water, and the crude white powder was purified by column chromatography (25 mL SiO₂, ethyl acetate: hexanes 10:90 to 2:5) to give 8 (0.2820 g, 89%) as a white crystalline solid: ¹H NMR (400 MHz, CDCl₃) δ 7.76 (d, J=15.6, 1H), 7.51 (dd, J=8.4, 2.0, 1H), 7.39 (d, J=2.4, 1H), 7.39 (s, 1H), 7.21 (s, 1H), 7.03 (d, J=8.4, 1H), 6.34, (d, J=16.0, 1H), 5.54 (s, 2H), 2.15 (s, 3H), 1.39 (s, 6H), 1.33 (s, 6H); ¹³C NMR (100.6 MHz, CDCl₃) δ 172.6, 155.2, 146.7, 143.4, 141.2, 134.2, 132.9, 132.8, 132.0, 130.8, 129.5, 128.6, 128.5, 128.0, 126.6, 115.9, 114.7, 60.4, 35.1, 35.0, 32.6, 32.5, 21.0, 19.4, 14.1; LC-MS (M+H)+ calcd for C₂₄H₂₇O₃ 363.1960, found 363.1967.

Example 5

Preparation of (E)-3-(4-(trifluoromethyl)-3-(1,2,3,4-tetrahydro-1,1,4,4,6-pentamethylnaphthalen-7-yl) phenyl)acrylic acid (9)

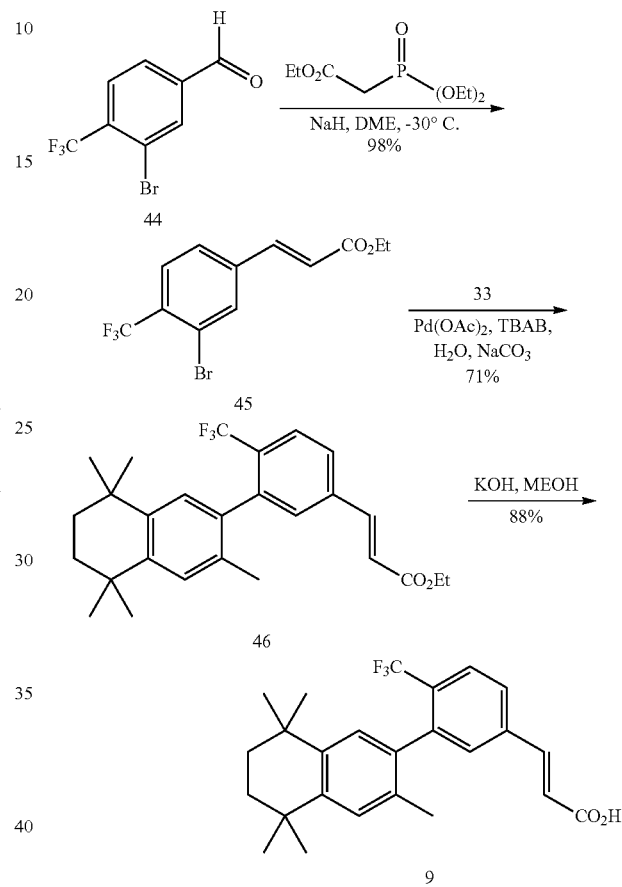

E)-ethyl 3-(3-bromo-4-(trifluoromethyl)phenyl)acrylate (45). To a solution of a 60% dispersion of NaH in mineral oil (0.31 g, 7.75 mmol) in DME (2 mL) at −30° C. was added a solution of ethyl 2-phosphonoacetate (1.46 mL, 7.29 mmol) in DME (13 mL), and the mixture was stirred at this temperature for 30 min. To this solution was added a solution of 3-bromo-4-(trifluoromethyl)benzaldehyde (44) (1.68 g, 6.63 mmol) in DME (3 mL), and the reaction was stirred at −30° C. for 1.5 h and then poured into water (50 mL) and extracted with ethyl acetate. The combined organic layers were washed with an aqueous saturated NH₄Cl solution and then brine, dried over sodium sulfate, filtered and concentrated in vacuo to give a crude product that was purified by column chromatography (150 mL SiO₂, ethyl acetate:hexanes 5:95) to give 45 (2.1188 g, 98%) as a colorless crystalline solid: ¹H NMR (400 MHz, CDCl₃) δ 7.84 (s, 1H), 7.69 (d, J=8.0, 1H), 7.59 (d, J=16.0, 1H), 7.52 (d, J=8.0, 1H), 6.50, (d, J=16.0, 1H), 4.27 (q, J=7.2, 2H), 1.34 (t, J=7.2, 3H); ¹³C NMR (100.6 MHz, CDCl₃) δ 165.9, 141.0, 139.2, 133.8, 131.4, 130.7, 130.4, 128.3, 128.2, 128.1, 128.1, 126.4, 123.9, 122.2, 121.2, 120.6, 120.5, 60.9, 14.2.

(E)-ethyl 3-(4-(trifluoromethyl)-3-(1,2,3,4-tetrahydro-1,1,4,4,6-pentamethylnaphthalen-7-yl)phenyl)acrylate (46). To a 50 mL Schlenk flask charged with bromide 45 (1.03 g, 3.20 mmol), boronic acid 33 (0.8040 g, 3.27 mmol), TBAB (1.04 g), Na$_2$CO$_3$ (1.02 g, 9.62 mmol), and water (7.4 mL), was added Pd(OAc)$_2$ (0.0406 g, 0.18 mmol), and the flask was evacuated and back-filled with nitrogen three times. The reaction was stirred at room temperature for 15 min and then placed in an oil bath pre-heated to 150° C. and stirred for 5 min. The reaction was allowed to cool to room temperature, and the black residue was taken up in ethyl acetate and water. The layers were separated, and the aqueous layer was extracted with ethyl acetate. The combined organic layers were washed with brine, dried over sodium sulfate, filtered, and concentrated in vacuo to give a crude product that was purified by column chromatography (150 mL SiO$_2$, ethyl acetate:hexanes 1:9) to give 46 (1.0138 g, 71%) as a colorless oil: $^1$H NMR (400 MHz, CDCl$_3$) δ 7.75 (d, J=8.4, 1H), 7.68 (d, J=16.0, 1H), 7.57 (d, J=8.0, 1H), 7.45 (s, 1H), 7.13 (s, 1H), 7.02 (s, 1H), 6.51 (d, J=16.0, 1H), 4.26 (q, J=7.2, 2H), 1.98 (s, 3H), 1.69 (s, 4H), 1.32 (t, J=7.2, 3H), 1.31 (s, 6H), 1.24 (s, 3H), 1.22 (s, 3H); $^{13}$C NMR (100.6 MHz, CDCl$_3$) δ 166.4, 144.5, 142.6, 141.9, 141.3, 137.1, 135.1, 132.3, 131.1, 130.2, 129.9, 127.6, 127.3, 126.7, 126.6, 126.3, 125.0, 122.3, 120.8, 60.7, 35.1, 35.0, 33.9, 33.8, 31.9, 31.8, 31.7, 19.7, 14.2.

(E)-3-(4-(trifluoromethyl)-3-(1,2,3,4-tetrahydro-1,1,4,4,6-pentamethylnaphthalen-7-yl)phenyl)acrylic acid (9). To a 100 mL round bottom flask containing 46 (0.4196 g, 1.00 mmol) suspended in methanol (5.0 mL) was added a solution of KOH (0.1706 g, 3.04 mmol) in water (0.22 mL), and the solution was refluxed in an oil-bath pre-heated to 85° C. for 1 h. The reaction was allowed to cool to room temperature, and acidified with an aqueous 20% HCl solution (33 mL). The resulting precipitate was filtered and washed with copious amounts of water, and the crude white powder was purified by column chromatography (25 mL SiO$_2$, ethyl acetate:hexanes 15:85) to give 9 (0.3445 g, 88%) as a white crystalline solid: $^1$H NMR (400 MHz, CDCl$_3$) δ 7.79 (d, J=15.6, 1H), 7.78 (d, J=8.4, 1H), 7.61 (d, J=8.4, 1H), 7.48 (s, 1H), 7.15 (s, 1H), 7.03 (s, 1H), 6.52, (d, J=16.0, 1H), 2.00 (s, 3H), 1.70 (s, 4H), 1.36 (s, 6H), 1.25 (s, 3H), 1.23 (s, 3H); $^{13}$C NMR (100.6 MHz, CDCl$_3$) δ 171.7, 145.2, 144.6, 142.1, 141.3, 136.6, 134.9, 132.3, 131.4, 130.7, 130.4, 127.6, 127.3, 126.7, 126.6, 124.9, 122.2, 119.8, 35.1, 35.0, 34.0, 33.8, 31.9, 31.8, 31.7, 19.7.

Example 6

Preparation of 2-fluoro-4-(1-(1,4-dihydro-1,1,4,4,6-pentamethylnaphthalen-7-yl)vinyl)benzoic acid (50)

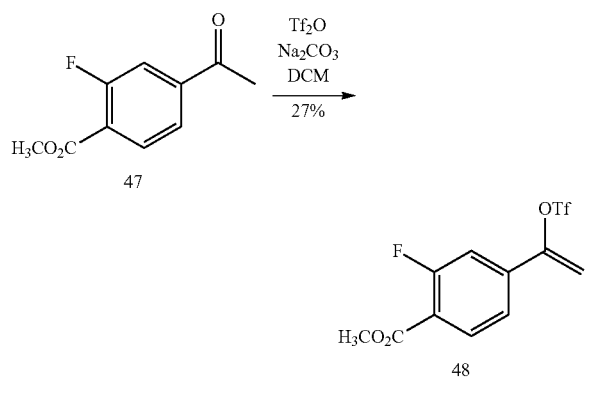

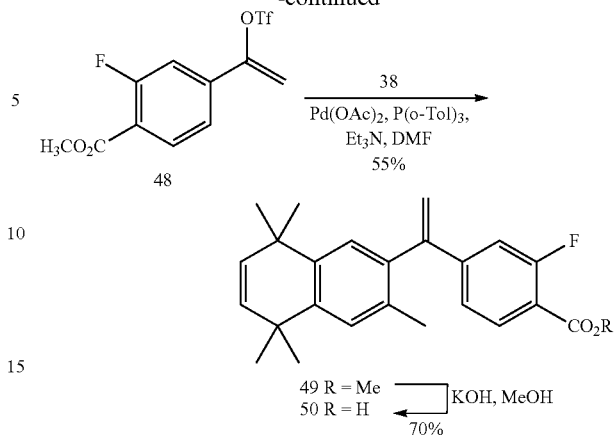

1-(4-(methoxycarbonyl)-3-fluorophenyl)vinyl trifluoromethanesulfonate (48). Following a procedure similar to that used by Faul and co-workers, to a solution of methyl 4-acetyl-2-fluorobenzoate (47) (1.972 g, 10.05 mmol) in dichloromethane (15.0 mL) was added finely ground anhydrous Na$_2$CO$_3$ (1.71 g, 16.1 mmol) followed by trifluoromethanesulfonic anhydride (3.4 mL, 20 mmol). The reaction was stirred under nitrogen for 24 h at which point an additional amount of finely ground anhydrous Na$_2$CO$_3$ (0.42 g, 4.0 mmol) followed by trifluoromethanesulfonic anhydride (1.7 mL, 10 mmol) was added, and the reaction was stirred for an additional 48 h. The mixture was filtered, concentrated in vacuo to an oil and loaded directly onto a silica gel column (2.5% ethyl acetate in hexanes). The product-containing fractions were combined to give 48 as a crystalline solid (0.9011 g, 27%): $^1$H NMR (400 MHz, CDCl$_3$) δ 8.00 (t, J=8.0, 1H), 7.38 (dd, J=8.0, 1.6, 1H), 7.31 (dd, J=11.2, 1.6, 1H), 5.76 (d, J=4.0, 1H), 5.55 (d, J=4.4, 1H), 3.94 (s, 3H); $^{13}$C NMR (100.6 MHz, CDCl$_3$) δ 163.9, 163.9, 163.1, 160.5, 150.9, 150.9, 137.9, 137.8, 132.9, 120.6, 120.5, 120.0, 119.9, 116.8, 114.0, 113.8, 107.4, 52.6; LC-MS (M)+ calcd for C$_{11}$H$_9$F$_4$O$_5$S 329.0107, found 329.0106.

methyl 2-fluoro-4-(1-(1,4-dihydro-1,1,4,4,6-pentamethylnaphthalen-7-yl)vinyl)benzoate (49). The method of Faul and co-workers was followed. A solution of boronic acid (38) (0.294 g, 1.20 mmols), triflate 48 (0.429 g, 1.31 mmols), Pd(OAc)$_2$ (0.014 g, 0.062 mmols), P(o-Tol)$_3$ (0.030 g, 0.099 mmols), and Et$_3$N (0.34 mL, 2.4 mmols) in DMF (4.0 mL) was heated to 50° C. and stirred for 2 h. After cooling to room temperature, the reaction was poured into water and extracted with ethyl acetate. The combined organic layers were washed with water, brine, and then dried over sodium sulfate, filtered and concentrated in vacuo to give a crude oil that was purified by column chromatography (silica gel, 2.5% ethyl acetate in hexanes) to give 49 as a white, crystalline solid: (0.252 g, 55%): $^1$H NMR (400 MHz, CDCl$_3$) δ 7.88 (t, J=8.0, 1H). 7.17-7.14 (m, 3H), 7.03 (dd, J=12.4, 1.6, 1H), 5.85 (d, J=1.2, 1H), 5.53 (s, 2H), 5.39 (d, J=1.2, 1H), 3.92 (s, 3H), 1.98 (s, 3H), 1.37 (s, 6H), 1.34 (s, 3H); $^{13}$C NMR (100.6 MHz, CDCl$_3$) δ 164.7, 164.7, 163.3, 160.7, 148.0, 147.9, 147.7, 147.6, 142.3, 140.2, 137.6, 133.0, 133.0, 1132.0, 127.8, 127.6, 122.0, 122.0, 117.8, 117.1, 117.0, 114.9, 114.7, 52.2, 35.0, 34.9, 32.6, 32.6, 19.9; LC-MS (M+H)+ calcd for C$_{25}$H$_{28}$FO$_2$ 379.2073, found 379.2069.

2-fluoro-4-(1-(1,4-dihydro-1,1,4,4,6-pentamethylnaphthalen-7-yl)vinyl)benzoic acid (50). To a suspension of 49 (0.2475 g, 0.65 mmol) in methanol (3.4 mL) was added a solution of KOH (0.1009 g) in water (0.18 mL), and the reaction was refluxed at 85° C. for 1 h. The reaction solution was cooled to room temperature and quenched with 1N HCl (50 mL). The crude precipitate was filtered and dried to give a crude white product (0.2135 g, 89%) that purified by column chromatography (silica gel, 10% to 30% ethyl acetate in hexanes) to give 50 as a crystalline solid (0.1664 g, 70%): $^1$H NMR (400 MHz, CDCl$_3$) δ 11.29 (br s, 1H), 7.97 (t, J=8.0, 1H), 7.20-7.16 (m, 3H), 7.07 (dd, J=12.4, 1.2, 1H), 5.88 (d, J=0.8, 1H), 5.54 (s, 2H), 5.42 (d, J=0.8, 1H), 2.00 (s, 3H), 1.37 (s, 6H), 1.34 (s, 6H); $^{13}$C NMR (100.6 MHz, CDCl$_3$) δ 169.5, 169.4, 164.0, 161.4, 148.8, 148.7, 147.9, 142.4, 140.2, 137.5, 133.0, 133.0, 132.7, 127.8, 127.6, 122.1, 122.1, 118.3, 116.0, 115.9, 115.1, 114.8, 35.0, 34.9, 32.6, 32.6, 19.9; LC-MS (M+H)+ calcd for C$_{24}$H$_{26}$O$_2$F 365.1917, found 365.1923. Anal. Calcd for C$_{24}$H$_{25}$O$_2$F: C, 79.09; H, 6.91; F, 5.21. Found: C, 78.74; H, 6.76; F, 5.10.

Example 7

Preparation of (E)-3-(4-(1,2,3,4-tetrahydro-1,1,4,4,6-pentamethylnaphthalen-7-yl)-5-methylpyridin-2-yl)acrylic acid (67)

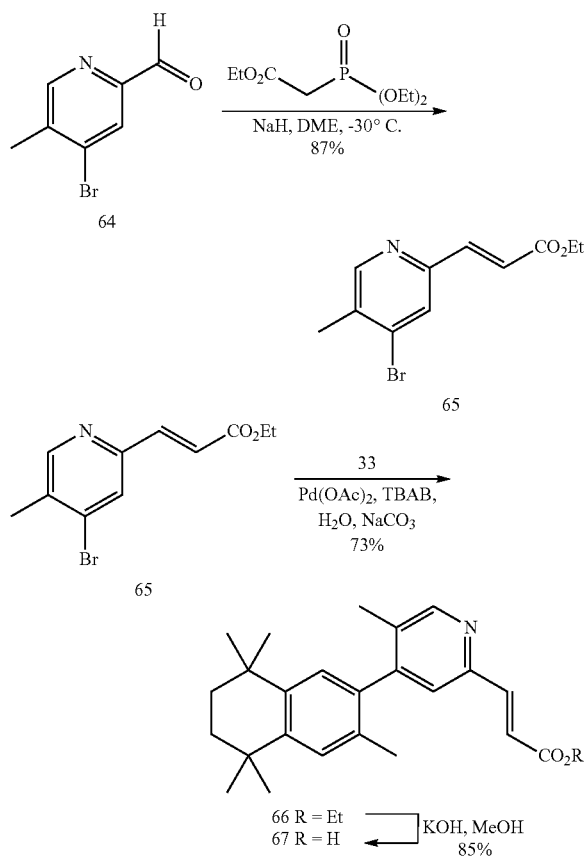

(E)-ethyl 3-(4-bromo-5-methylpyridin-2-yl)acrylate (65). To a solution of a 60% dispersion of NaH in mineral oil (0.29 g, 7.25 mmol) in DME (2 mL) at −30° C. was added a solution of ethyl 2-phosphonoacetate (1.46 mL, 7.29 mmol) in DME (13 mL), and the mixture was stirred at this temperature for 30 min. To this solution was added a solution of 4-bromo-5-methylpyridine-2-carbaldehyde (64) (1.32 g, 6.60 mmol) in DME (3 mL), and the reaction was stirred at −30° C. for 1.5 h and then poured into water (50 mL) and extracted with ethyl acetate. The combined organic layers were washed with an aqueous saturated NH$_4$Cl solution and then brine, dried over sodium sulfate, filtered and concentrated in vacuo to give a crude product that was purified by column chromatography (150 mL SiO$_2$, ethyl acetate:hexanes 1:9) to give 65 (1.553 g, 87%) as a colorless crystalline solid: $^1$H NMR (400 MHz, CDCl$_3$) δ 8.41 (s, 1H), 7.59 (d, J=15.6, 1H), 7.58 (s, 1H), 6.88 (d, J=15.6, 1H), 4.25 (q, J=7.2, 2H), 2.38 (s, 3H), 1.31 (t, J=7.2, 3H); $^{13}$C NMR (100.6 MHz, CDCl$_3$) δ 166.4, 151.6, 150.8, 141.6, 135.4, 134.7, 127.3, 122.9, 60.6, 19.4, 14.2.

(E)-ethyl 3-(4-(1,2,3,4-tetrahydro-1,1,4,4,6-pentamethylnaphthalen-7-yl)-5-methylpyridin-2-yl)acrylate (66). To a 50 mL Schlenk flask charged with bromide 65 (0.434 g, 1.61 mmol), boronic acid 33 (0.4010 g, 1.63 mmol), TBAB (0.52 g), Na$_2$CO$_3$ (0.51 g, 4.81 mmol), and water (3.7 mL), was added Pd(OAc)$_2$ (0.0203 g, 0.09 mmol), and the flask was evacuated and back-filled with nitrogen three times. The reaction was stirred at room temperature for 15 min and then placed in an oil bath pre-heated to 150° C. and stirred for 5 min. The reaction was allowed to cool to room temperature, and the black residue was taken up in ethyl acetate and water. The layers were separated, and the aqueous layer was extracted with ethyl acetate. The combined organic layers were washed with brine, dried over sodium sulfate, filtered, and concentrated in vacuo to give a crude product that was purified by column chromatography (150 mL SiO$_2$, ethyl acetate:hexanes 1:9) to give 66 (0.4602 g, 73%) as a white solid: $^1$H NMR (400 MHz, CDCl$_3$) δ 8.52 (s, 1H), 7.69 (d, J=16.0, 1H), 7.24 (s, 1H), 7.18 (s, 1H), 6.95 (s, 1H), 6.90 (d, J=16.0, 1H), 4.25 (q, J=7.2, 2H), 2.10 (s, 3H), 2.00 (s, 3H), 1.69 (s, 4H), 1.33 (t, J=7.2, 3H), 1.32 (s, 6H), 1.24 (s, 6H); $^{13}$C NMR (100.6 MHz, CDCl$_3$) δ 166.8, 151.2, 150.6, 150.3, 144.7, 143.3, 142.5, 135.2, 132.9, 131.6, 128.0, 126.4, 124.8, 121.5, 60.5, 35.1, 35.0, 34.0, 33.9, 31.9, 31.8, 19.3, 16.8, 14.2.

(E)-3-(4-(1,2,3,4-tetrahydro-1,1,4,4,6-pentamethylnaphthalen-7-yl)-5-methylpyridin-2-yl)acrylic acid (67). To a 100 mL round bottom flask containing 66 (0.8896 g, 2.27 mmol) suspended in methanol (7.0 mL) was added a solution of KOH (0.382 g, 6.81 mmol) in water (0.50 mL), and the solution was refluxed in an oil-bath pre-heated to 85° C. for 1 hour. The reaction was allowed to cool to room temperature, and acidified with an aqueous 20% HCl solution (60 mL). The resulting precipitate was filtered and washed with copious amounts of water, and the crude white powder that appeared to be pure by TLC (single spot) 67 (0.7041 g, 85%) as a white crystalline solid: $^1$H NMR (400 MHz, methanol-d4) δ 8.82 (s, 1H), 8.16 (s, 1H), 7.80 (d, J=16.4, 1H), 7.38 (s, 1H), 7.16 (s, 1H), 7.13 (d, J=16.0, 1H), 2.32 (s, 3H), 2.11 (s, 3H), 1.77 (s, 4H), 1.35 (d, J=9.6, 6H), 1.31 (d, 6H); $^{13}$C NMR (100.6 MHz, methanol-d4) δ 167.6, 161.8, 147.7, 146.3, 144.3, 144.0, 138.7, 135.0, 134.6, 132.6, 130.1, 129.9, 127.7, 127.1, 36.0, 35.1, 35.0, 32.3, 32.2, 32.1, 19.3, 17.3.

Example 8

Preparation of (E)-3-(5-(1,2,3,4-tetrahydro-1,1,4,4,6-pentamethylnaphthalen-7-yl)-6-methylpyridin-3-yl)acrylic acid (71)

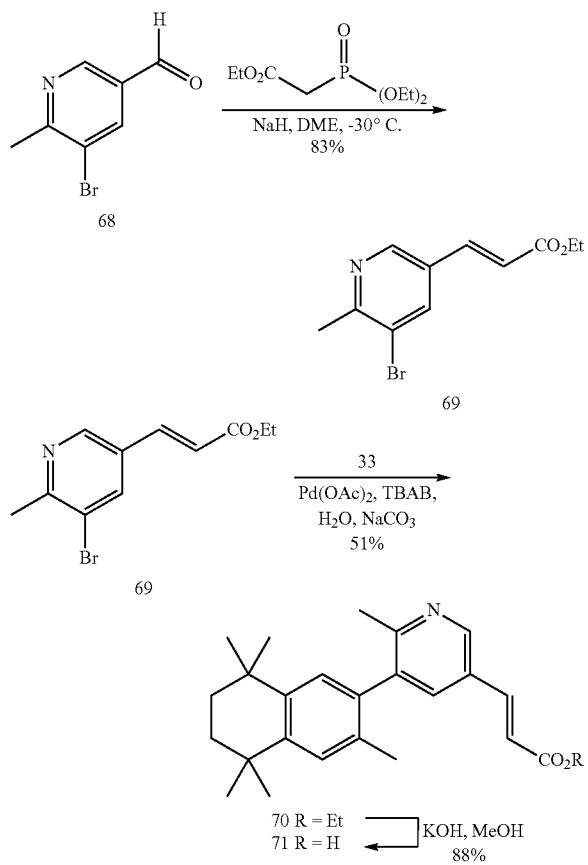

(E)-ethyl 3-(5-bromo-6-methylpyridin-3-yl)acrylate (69). To a solution of a 60% dispersion of NaH in mineral oil (0.29 g, 7.25 mmol) in DME (2 mL) at −30° C. was added a solution of ethyl 2-phosphonoacetate (1.46 mL, 7.29 mmol) in DME (13 mL), and the mixture was stirred at this temperature for 30 min. To this solution was added a solution of 5-bromo-6-methylpyridine-3-carbaldehyde (68) (1.35 g, 6.75 mmol) in DME (3 mL), and the reaction was stirred at −30° C. for 1.5 h and then poured into water (50 mL) and extracted with ethyl acetate. The combined organic layers were washed with an aqueous saturated $NH_4Cl$ solution and then brine, dried over sodium sulfate, filtered and concentrated in vacuo to give a crude product that was purified by column chromatography (150 mL $SiO_2$, ethyl acetate:hexanes 1:9) to give 69 (1.487 g, 83%) as a colorless crystalline solid: $^1$H NMR (400 MHz, $CDCl_3$) δ 8.52 (d, J=2.0, 1H), 7.96 (d, J=2.0, 1H), 7.59 (d, J=16.0, 1H), 6.47 (d, J=15.6, 1H), 4.26 (q, J=7.2, 2H), 2.67 (s, 3H), 1.32 (t, J=7.2, 3H); $^{13}$C NMR (100.6 MHz, $CDCl_3$) δ 166.0, 158.9, 147.1, 139.1, 137.6, 129.5, 121.7, 120.8, 60.8, 24.9, 14.2.

(E)-ethyl 3-(5-(1,2,3,4-tetrahydro-1,1,4,4,6-pentamethylnaphthalen-7-yl)-6-methylpyridin-3-yl)acrylate (70). To a 50 mL Schlenk flask charged with bromide 69 (0.434 g, 1.61 mmol), boronic acid 33 (0.4010 g, 1.63 mmol), TBAB (0.52 g), $Na_2CO_3$ (0.51 g, 4.81 mmol), and water (3.7 mL), was added $Pd(OAc)_2$ (0.0203 g, 0.09 mmol), and the flask was evacuated and back-filled with nitrogen three times. The reaction was stirred at room temperature for 15 min and then placed in an oil bath pre-heated to 150° C. and stirred for 5 min. The reaction was allowed to cool to room temperature, and the black residue was taken up in ethyl acetate and water. The layers were separated, and the aqueous layer was extracted with ethyl acetate. The combined organic layers were washed with brine, dried over sodium sulfate, filtered, and concentrated in vacuo to give a crude product that was purified by column chromatography (150 mL $SiO_2$, ethyl acetate:hexanes 1:9) to give 70 (0.323 g, 51%) as a white solid: $^1$H NMR (400 MHz, $CDCl_3$) δ 8.61 (d, J=2.0, 1H), 7.79 (d, J=16.0, 1H), 7.63 (d, J=2.4, 1H), 7.18 (s, 1H), 6.99 (s, 1H), 6.48 (d, J=16.0, 1H), 4.25 (q, J=7.2, 2H), 2.34 (s, 3H), 2.01 (s, 3H), 1.70 (s, 4H), 1.32 (t, J=7.2, 3H), 1.31 (s, 6H), 1.25 (d, J=7.2, 6H); $^{13}$C NMR (100.6 MHz, $CDCl_3$) δ 166.4, 158.6, 147.5, 144.7, 142.5, 140.9, 137.2, 135.5, 135.3, 132.2, 128.0, 127.5, 127.2, 119.4, 60.6, 35.1, 35.0, 34.0, 33.9, 31.9, 31.8, 31.8, 22.9, 19.5, 14.2.

(E)-3-(5-(1,2,3,4-tetrahydro-1,1,4,4,6-pentamethylnaphthalen-7-yl)-6-methylpyridin-3-yl)acrylic acid (71). To a 100 mL round bottom flask containing 70 (0.6000 g, 1.53 mmol) suspended in methanol (4.8 mL) was added a solution of KOH (0.2581 g, 4.60 mmol) in water (0.34 mL), and the solution was refluxed in an oil-bath pre-heated to 85° C. for 1 h. The reaction was allowed to cool to room temperature, and acidified with an aqueous 20% HCl solution (42 mL). The resulting precipitate was filtered and washed with copious amounts of water, and the crude white powder that appeared to be pure by TLC (single spot) 71 (0.4943 g, 88%) as a white crystalline solid: $^1$H NMR (400 MHz, methanol-d4) δ 8.91 (d, J=2.0, 1H), 8.41 (d, J=2.0, 1H), 7.79 (d, J=16.4, 1H), 7.33 (s, 1H), 7.16 (s, 1H), 6.81 (d, J=16.0, 1H), 2.48 (s, 3H), 2.07 (s, 3H), 1.73 (s, 4H), 1.33 (d, J=10.4, 6H), 1.27 (s, 6H); $^{13}$C NMR (100.6 MHz, methanol-d4) δ 168.8, 155.6, 147.3, 144.3, 143.4, 142.5, 141.9, 139.0, 133.9, 133.6, 132.5, 129.8, 128.4, 125.0, 36.1, 36.1, 35.1, 35.0, 32.3, 32.2, 32.1, 19.6, 19.5.

Example 9

The following illustrate representative pharmaceutical dosage forms, containing a compound of the invention, or a salt thereof ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for inhibiting cancer cell growth comprising contacting the cell in vitro or in vivo with an effective amount of a compound of formula II:

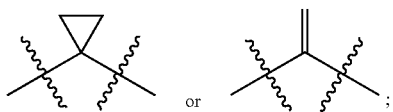

or a salt thereof wherein:
R$^1$ is H, or (C$_1$-C$_6$)alkyl, wherein each (C$_1$-C$_6$)alkyl, that is optionally substituted with one or more groups independently selected from halo;

the bond represented by --- is a single bond or a double bond;
D is

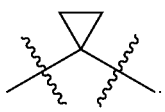 [SMILES: *C1(*)CC1]

R$^2$ is COOH; and R$^3$ and R$^4$ are each H;
wherein the cancer is colon cancer.

2. The method of claim 1, wherein the bond represented by --- is a single bond.

3. The method of claim 1, wherein the bond represented by --- is a double bond.

4. The method of claim 1, wherein D is

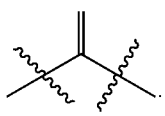 [SMILES: *C(*)=C]

5. The method of claim 1, wherein D is

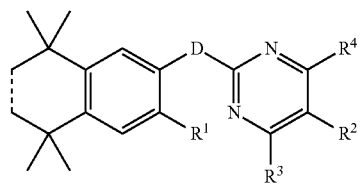

6. A method for inhibiting cancer cell growth comprising contacting the cell in vitro or in vivo with an effective amount of the compound:

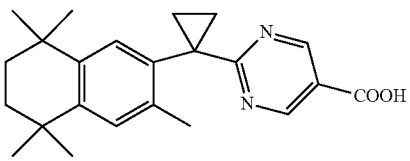 [SMILES: Cc1cc2c(cc1C1(c3ncc(C(=O)O)cn3)CC1)C(C)(C)CCC2(C)C]

or a pharmaceutically acceptable salt thereof, wherein the cancer is colon cancer.

7. A method for inhibiting cancer cell growth comprising contacting the cell in vitro or in vivo with an effective amount of a compound selected from the group consisting of:

1

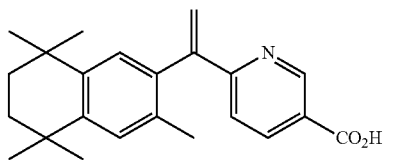

2

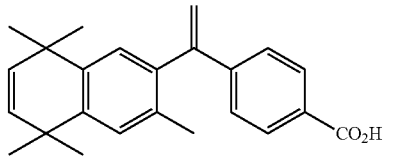

-continued
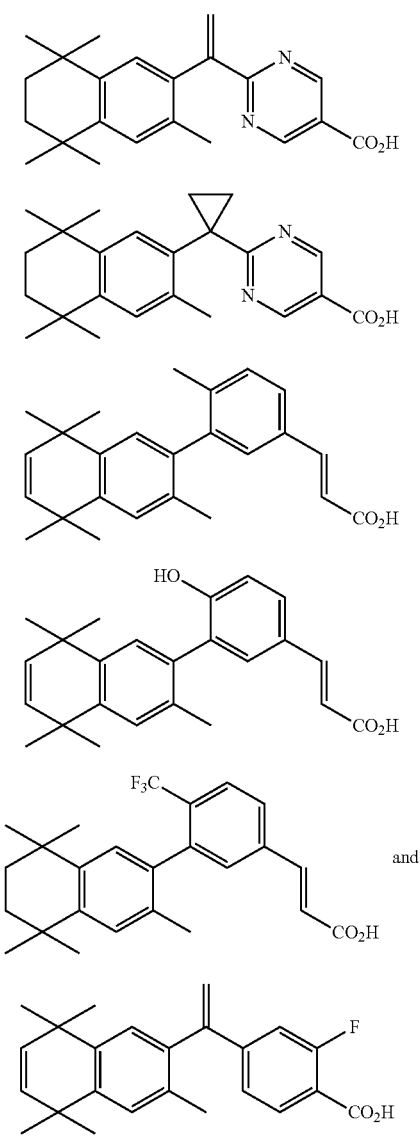
or a pharmaceutically acceptable salt thereof; wherein the cancer is colon cancer.
8. A method for inhibiting cancer cell growth comprising contacting the cell in vitro or in vivo with an effective amount of a compound selected from the group consisting of:
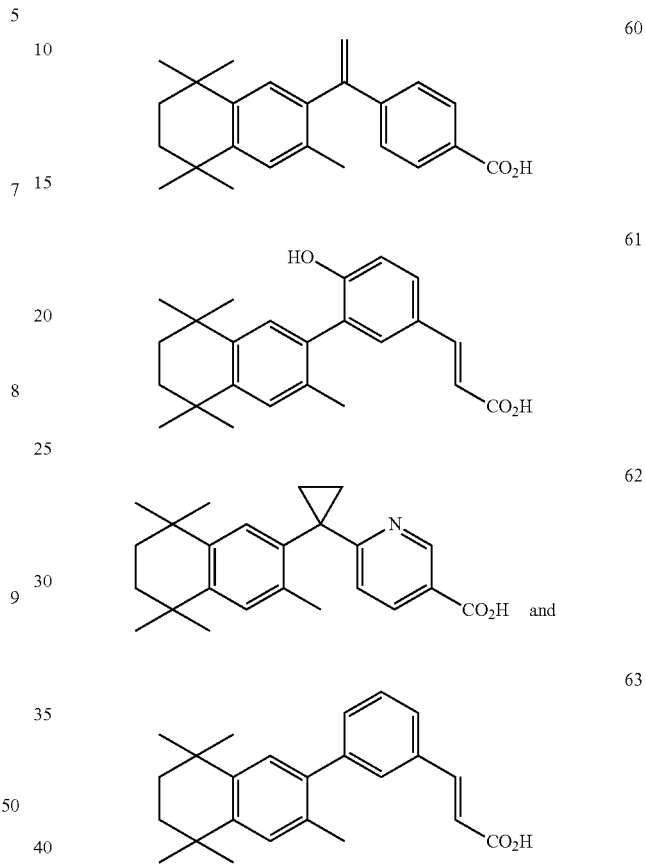
or a pharmaceutically acceptable salt thereof; wherein the cancer is colon cancer.
* * * * *

UNITED STATES PATENT AND TRADEMARK OFFICE
CERTIFICATE OF CORRECTION

PATENT NO. : 10,391,093 B2  
APPLICATION NO. : 15/398584  
DATED : August 27, 2019  
INVENTOR(S) : Carl E. Wagner, Peter W. Jurutka and Pamela A. Marshall Page 1 of 1

It is certified that error appears in the above-identified patent and that said Letters Patent is hereby corrected as shown below:

In the Specification

In Column 1, Line 15-18:
Please delete the following paragraph:
"This invention was made with government support under 1R15CA139364-01A2 awarded by NIH/National Cancer Institute. The government has certain rights in the invention."

Please insert the following paragraph:
-- This invention was made with government support under R15 CA139364 awarded by the National Institutes of Health. The government has certain rights in the invention. --

Signed and Sealed this
Twenty-fifth Day of February, 2020

Andrei Iancu
*Director of the United States Patent and Trademark Office*